(12) United States Patent
Belson

(10) Patent No.: US 9,522,254 B2
(45) Date of Patent: Dec. 20, 2016

(54) SYSTEMS AND METHODS FOR VENIPUNCTURE AND CATHETER PLACEMENT

(71) Applicant: Vascular Pathways, Inc., Naples, FL (US)

(72) Inventor: Amir Belson, Los Altos, CA (US)

(73) Assignee: Vascular Pathways, Inc., Salt Lake City, UT (US)

( * ) Notice: Subject to any disclaimer, the term of this patent is extended or adjusted under 35 U.S.C. 154(b) by 104 days.

(21) Appl. No.: 14/167,149

(22) Filed: Jan. 29, 2014

(65) Prior Publication Data

US 2014/0214005 A1    Jul. 31, 2014

Related U.S. Application Data

(60) Provisional application No. 61/758,517, filed on Jan. 30, 2013, provisional application No. 61/772,980, filed on Mar. 5, 2013.

(51) Int. Cl.
*A61M 31/00* (2006.01)
*A61M 25/06* (2006.01)
*A61M 25/09* (2006.01)

(52) U.S. Cl.
CPC ...... *A61M 25/0606* (2013.01); *A61M 25/0637* (2013.01); *A61M 25/0693* (2013.01); *A61M 25/09* (2013.01)

(58) Field of Classification Search
CPC .............. A61M 25/0606; A61M 25/0172; A61M 25/20693; A61M 25/09; A61M 25/0637

USPC ........................................................ 604/510
See application file for complete search history.

(56) References Cited

U.S. PATENT DOCUMENTS

| | | | |
|---|---|---|---|
| 2,211,975 | A | 8/1940 | Hendrickson |
| 2,259,488 | A | 10/1941 | Raiche |
| 2,330,400 | A | 9/1943 | Winder |
| D138,589 | S | 8/1944 | Brandenburg |
| 3,185,151 | A | 5/1965 | Czorny |
| 3,297,030 | A | 1/1967 | Czorny et al. |
| 3,416,567 | A | 12/1968 | von Dardel et al. |
| 3,469,579 | A | 9/1969 | Hubert |
| 3,500,828 | A | 3/1970 | Podhora |
| 3,552,384 | A | 1/1971 | Pierie et al. |
| 3,572,334 | A | 3/1971 | Petterson |

(Continued)

FOREIGN PATENT DOCUMENTS

| | | |
|---|---|---|
| AU | 710967 B2 | 9/1999 |
| CN | 1178707 A | 4/1998 |

(Continued)

OTHER PUBLICATIONS

International search report and written opinion dated Apr. 14, 2014 for PCT Application No. US2014/013557.

(Continued)

*Primary Examiner* — Edelmira Bosques
(74) *Attorney, Agent, or Firm* — Rutan & Tucker, LLP

(57) ABSTRACT

Intravenous access is achieved by introducing a catheter having a guidewire safety tip at its distal end. The safety tip can be advanced and retracted using a slider disposed over an access needle which is initially present in the catheter. After the catheter has been properly positioned, the access needle and guidewire may be removed so that the catheter is available for use.

18 Claims, 11 Drawing Sheets

(56) References Cited

U.S. PATENT DOCUMENTS

| | | |
|---|---|---|
| 3,585,996 A | 6/1971 | Reynolds et al. |
| 3,589,361 A | 6/1971 | Loper et al. |
| 3,592,192 A | 7/1971 | Harautuneian |
| 3,595,230 A | 7/1971 | Suyeoka et al. |
| 3,610,240 A | 10/1971 | Harautuneian |
| 3,682,173 A | 8/1972 | Center |
| 3,884,242 A | 5/1975 | Bazell et al. |
| 3,921,631 A | 11/1975 | Thompson |
| 3,995,628 A | 12/1976 | Gula et al. |
| 4,027,668 A | 6/1977 | Dunn |
| 4,037,600 A | 7/1977 | Poncy et al. |
| 4,079,738 A | 3/1978 | Dunn et al. |
| 4,106,506 A | 8/1978 | Koehn et al. |
| 4,177,809 A | 12/1979 | Moorehead |
| 4,292,970 A | 10/1981 | Hession, Jr. |
| 4,317,445 A | 3/1982 | Robinson |
| 4,345,602 A | 8/1982 | Yoshimura et al. |
| 4,354,491 A | 10/1982 | Marbry |
| 4,368,730 A | 1/1983 | Sharrock |
| 4,387,879 A | 6/1983 | Tauschinski |
| 4,417,886 A | 11/1983 | Frankhouser et al. |
| 4,449,693 A | 5/1984 | Gereg |
| 4,464,171 A | 8/1984 | Garwin |
| 4,509,534 A | 4/1985 | Tassin, Jr. |
| 4,509,945 A | 4/1985 | Kramann et al. |
| 4,511,359 A | 4/1985 | Vaillancourt |
| 4,512,766 A | 4/1985 | Vailancourt |
| 4,581,019 A | 4/1986 | Curelaru et al. |
| 4,585,440 A | 4/1986 | Tchervenkov et al. |
| D287,877 S | 1/1987 | Holewinski et al. |
| 4,728,322 A | 3/1988 | Walker et al. |
| 4,738,659 A | 4/1988 | Sleiman |
| 4,747,831 A | 5/1988 | Kulli |
| 4,767,407 A | 8/1988 | Foran |
| 4,772,264 A | 9/1988 | Cragg |
| 4,772,267 A | 9/1988 | Brown |
| 4,781,703 A | 11/1988 | Walker et al. |
| 4,792,531 A | 12/1988 | Kakihana |
| 4,798,193 A | 1/1989 | Giesy et al. |
| 4,813,934 A | 3/1989 | Engelson et al. |
| 4,826,070 A | 5/1989 | Kakihana |
| 4,828,547 A | 5/1989 | Sahi et al. |
| 4,834,708 A | 5/1989 | Pillari |
| 4,834,718 A | 5/1989 | McDonald |
| 4,840,613 A | 6/1989 | Balbierz |
| 4,840,622 A | 6/1989 | Hardy |
| 4,842,591 A | 6/1989 | Luther |
| 4,846,812 A | 7/1989 | Walker et al. |
| 4,869,259 A | 9/1989 | Elkins |
| D304,079 S | 10/1989 | McFarlane |
| 4,871,358 A | 10/1989 | Gold |
| 4,874,377 A | 10/1989 | Newgard et al. |
| 4,883,461 A | 11/1989 | Sawyer |
| 4,883,699 A | 11/1989 | Aniuk et al. |
| 4,894,052 A | 1/1990 | Crawford |
| 4,895,346 A | 1/1990 | Steigerwald |
| 4,900,307 A | 2/1990 | Kulli |
| 4,906,956 A | 3/1990 | Kakihana |
| 4,908,021 A | 3/1990 | McFarlane |
| 4,909,793 A | 3/1990 | Vining et al. |
| 4,911,691 A | 3/1990 | Aniuk et al. |
| 4,913,704 A | 4/1990 | Kurimoto |
| 4,917,102 A | 4/1990 | Miller et al. |
| 4,917,671 A | 4/1990 | Chang |
| 4,929,235 A | 5/1990 | Merry et al. |
| 4,935,010 A | 6/1990 | Cox et al. |
| 4,944,725 A | 7/1990 | McDonald |
| 4,944,728 A | 7/1990 | Carrell et al. |
| 4,955,863 A | 9/1990 | Walker et al. |
| 4,961,729 A | 10/1990 | Vaillancourt |
| 4,966,586 A | 10/1990 | Vaillancourt |
| 4,966,589 A | 10/1990 | Kaufman |
| 4,994,042 A | 2/1991 | Vadher |
| 4,994,047 A | 2/1991 | Walker et al. |
| 4,995,866 A | 2/1991 | Amplatz et al. |
| 5,007,901 A | 4/1991 | Shields |
| 5,009,642 A | 4/1991 | Sahi |
| 5,019,048 A | 5/1991 | Margolin |
| 5,019,049 A | 5/1991 | Haining |
| D318,733 S | 7/1991 | Wyzgala |
| 5,034,347 A | 7/1991 | Kakihana |
| 5,047,013 A | 9/1991 | Rossdeutscher |
| D321,250 S | 10/1991 | Jepson et al. |
| 5,053,014 A | 10/1991 | Van Heugten |
| 5,054,501 A | 10/1991 | Chuttani et al. |
| 5,061,254 A | 10/1991 | Karakelle et al. |
| 5,064,416 A | 11/1991 | Newgard et al. |
| 5,078,694 A | 1/1992 | Wallace |
| 5,078,696 A | 1/1992 | Nedbaluk |
| 5,078,702 A | 1/1992 | Pomeranz |
| 5,084,023 A | 1/1992 | Lemieux |
| 5,085,645 A | 2/1992 | Purdy et al. |
| 5,088,984 A | 2/1992 | Fields |
| 5,093,692 A | 3/1992 | Su et al. |
| 5,098,392 A | 3/1992 | Fleischhacker et al. |
| 5,098,395 A | 3/1992 | Fields |
| 5,098,405 A | 3/1992 | Peterson et al. |
| 5,108,375 A | 4/1992 | Harrison et al. |
| 5,108,376 A | 4/1992 | Bonaldo |
| 5,112,312 A | 5/1992 | Luther |
| 5,116,323 A | 5/1992 | Kreuzer et al. |
| 5,120,317 A | 6/1992 | Luther |
| 5,125,906 A | 6/1992 | Fleck |
| 5,135,487 A | 8/1992 | Morrill et al. |
| 5,137,515 A | 8/1992 | Hogan |
| 5,149,326 A | 9/1992 | Woodgrift et al. |
| 5,154,703 A | 10/1992 | Bonaldo |
| 5,156,590 A | 10/1992 | Vilmar |
| 5,156,596 A | 10/1992 | Balbierz et al. |
| 5,158,544 A | 10/1992 | Weinstein |
| 5,167,637 A | 12/1992 | Okada et al. |
| 5,176,650 A | 1/1993 | Haining |
| 5,186,168 A | 2/1993 | Spofford et al. |
| 5,186,712 A | 2/1993 | Kelso et al. |
| 5,188,607 A | 2/1993 | Wu |
| 5,190,528 A | 3/1993 | Fonger et al. |
| 5,192,301 A | 3/1993 | Kamiya et al. |
| 5,195,974 A | 3/1993 | Hardy |
| 5,195,980 A | 3/1993 | Catlin |
| 5,195,985 A | 3/1993 | Hall |
| 5,205,830 A | 4/1993 | Dassa et al. |
| 5,215,527 A | 6/1993 | Beck et al. |
| 5,215,528 A | 6/1993 | Purdy et al. |
| 5,217,435 A | 6/1993 | Kring |
| 5,219,335 A | 6/1993 | Willard et al. |
| 5,221,255 A | 6/1993 | Mahurkar et al. |
| 5,222,944 A | 6/1993 | Harris |
| 5,225,369 A | 7/1993 | Su et al. |
| 5,226,899 A | 7/1993 | Lee et al. |
| D338,955 S | 8/1993 | Gresl et al. |
| 5,234,410 A | 8/1993 | Graham et al. |
| 5,242,411 A | 9/1993 | Yamamoto et al. |
| 5,246,426 A | 9/1993 | Lewis et al. |
| 5,246,430 A | 9/1993 | MacFarlane |
| 5,254,107 A | 10/1993 | Soltesz |
| 5,257,980 A | 11/1993 | Van Antwerp et al. |
| 5,267,982 A | 12/1993 | Sylvanowicz |
| 5,269,771 A | 12/1993 | Thomas et al. |
| D345,419 S | 3/1994 | Horrigan et al. |
| 5,290,310 A | 3/1994 | Makower et al. |
| 5,297,546 A | 3/1994 | Spofford et al. |
| 5,312,359 A | 5/1994 | Wallace |
| 5,312,361 A | 5/1994 | Zadini et al. |
| 5,320,608 A | 6/1994 | Gerrone |
| 5,322,517 A | 6/1994 | Sircom et al. |
| 5,330,435 A | 7/1994 | Vaillancourt |
| 5,334,159 A | 8/1994 | Turkel |
| 5,338,311 A | 8/1994 | Mahurkar |
| 5,352,205 A | 10/1994 | Dales et al. |
| 5,358,796 A | 10/1994 | Nakamura et al. |
| 5,366,441 A | 11/1994 | Crawford |
| 5,368,661 A | 11/1994 | Nakamura et al. |
| D353,668 S | 12/1994 | Banks et al. |
| 5,376,082 A | 12/1994 | Phelps |

(56) References Cited

U.S. PATENT DOCUMENTS

| | | |
|---|---|---|
| 5,376,094 A | 12/1994 | Kline |
| 5,380,290 A | 1/1995 | Makower et al. |
| 5,395,341 A | 3/1995 | Slater |
| 5,397,311 A | 3/1995 | Walker et al. |
| 5,405,323 A | 4/1995 | Rogers et al. |
| 5,415,177 A | 5/1995 | Zadini et al. |
| 5,415,645 A | 5/1995 | Friend et al. |
| 5,419,766 A | 5/1995 | Chang et al. |
| 5,419,777 A | 5/1995 | Hofling |
| 5,423,760 A | 6/1995 | Yoon |
| 5,425,718 A | 6/1995 | Tay et al. |
| 5,431,506 A | 7/1995 | Masunaga |
| 5,445,625 A | 8/1995 | Voda |
| 5,454,785 A | 10/1995 | Smith |
| 5,454,790 A | 10/1995 | Dubrul |
| 5,456,258 A | 10/1995 | Kondo et al. |
| 5,456,668 A | 10/1995 | Ogle, II |
| 5,458,658 A | 10/1995 | Sircom |
| 5,466,230 A | 11/1995 | Davila |
| 5,480,389 A | 1/1996 | McWha et al. |
| 5,482,395 A | 1/1996 | Gasparini |
| 5,484,419 A | 1/1996 | Fleck |
| 5,487,734 A | 1/1996 | Thorne et al. |
| 5,489,273 A | 2/1996 | Whitney et al. |
| 5,496,281 A | 3/1996 | Krebs |
| 5,501,675 A | 3/1996 | Erskine |
| 5,507,300 A | 4/1996 | Mukai et al. |
| 5,512,052 A | 4/1996 | Jesch |
| 5,514,108 A | 5/1996 | Stevens |
| 5,520,655 A | 5/1996 | Davila et al. |
| 5,520,657 A * | 5/1996 | Sellers ............ A61M 25/06 600/575 |
| D371,195 S | 6/1996 | Krebs |
| 5,522,807 A | 6/1996 | Luther |
| 5,527,290 A | 6/1996 | Zadini et al. |
| 5,531,701 A | 7/1996 | Luther |
| 5,531,713 A | 7/1996 | Mastronardi et al. |
| 5,533,988 A | 7/1996 | Dickerson et al. |
| 5,535,785 A | 7/1996 | Werge et al. |
| 5,542,933 A | 8/1996 | Marks |
| 5,554,136 A | 9/1996 | Luther |
| 5,562,629 A | 10/1996 | Haughton et al. |
| 5,562,630 A | 10/1996 | Nichols |
| 5,562,631 A | 10/1996 | Bogert |
| 5,562,633 A | 10/1996 | Wozencroft et al. |
| 5,562,634 A | 10/1996 | Flumene et al. |
| 5,569,202 A | 10/1996 | Kovalic et al. |
| 5,569,217 A | 10/1996 | Luther |
| 5,571,073 A | 11/1996 | Castillo |
| 5,573,510 A | 11/1996 | Isaacson |
| 5,591,194 A | 1/1997 | Berthiaume |
| 5,599,291 A | 2/1997 | Balbierz et al. |
| 5,599,327 A | 2/1997 | Sugahara et al. |
| 5,609,583 A | 3/1997 | Hakki et al. |
| 5,613,663 A | 3/1997 | Schmidt et al. |
| 5,613,954 A | 3/1997 | Nelson et al. |
| 5,630,802 A | 5/1997 | Moellmann et al. |
| 5,630,823 A | 5/1997 | Schmitz-Rode et al. |
| 5,634,475 A | 6/1997 | Wolvek |
| 5,634,913 A | 6/1997 | Stinger |
| 5,637,091 A | 6/1997 | Hakky et al. |
| 5,645,076 A | 7/1997 | Yoon |
| 5,651,772 A | 7/1997 | Arnett |
| D383,538 S | 9/1997 | Erskine et al. |
| 5,662,622 A | 9/1997 | Gore et al. |
| 5,674,241 A | 10/1997 | Bley et al. |
| 5,676,658 A | 10/1997 | Erskine |
| 5,683,368 A | 11/1997 | Schmidt |
| 5,683,370 A | 11/1997 | Luther et al. |
| 5,685,855 A | 11/1997 | Erskine |
| 5,685,858 A | 11/1997 | Kawand |
| 5,685,860 A | 11/1997 | Chang et al. |
| 5,688,249 A | 11/1997 | Chang et al. |
| 5,693,025 A | 12/1997 | Stevens |
| 5,695,474 A | 12/1997 | Daugherty |
| 5,700,250 A | 12/1997 | Erskine |
| 5,702,369 A | 12/1997 | Mercereau |
| 5,704,914 A | 1/1998 | Stocking et al. |
| 5,722,425 A | 3/1998 | Bostrom |
| 5,725,503 A | 3/1998 | Arnett |
| 5,730,150 A | 3/1998 | Peppel et al. |
| 5,730,733 A | 3/1998 | Mortier et al. |
| 5,738,144 A | 4/1998 | Rogers |
| 5,738,660 A | 4/1998 | Luther |
| 5,743,882 A | 4/1998 | Luther |
| 5,743,888 A | 4/1998 | Wilkes et al. |
| 5,749,371 A | 5/1998 | Zadini et al. |
| 5,749,857 A | 5/1998 | Cuppy |
| 5,750,741 A | 5/1998 | Crocker et al. |
| 5,755,693 A | 5/1998 | Walker et al. |
| 5,755,709 A | 5/1998 | Cuppy |
| 5,762,630 A | 6/1998 | Bley et al. |
| 5,762,636 A | 6/1998 | Rupp et al. |
| 5,765,682 A | 6/1998 | Bley et al. |
| 5,779,679 A | 7/1998 | Shaw |
| 5,779,680 A | 7/1998 | Yoon |
| 5,779,681 A | 7/1998 | Bonn |
| 5,782,807 A | 7/1998 | Falvai et al. |
| D397,434 S | 8/1998 | Pike |
| 5,792,124 A | 8/1998 | Horrigan et al. |
| 5,800,395 A | 9/1998 | Botich et al. |
| 5,807,339 A | 9/1998 | Bostrom et al. |
| 5,807,342 A | 9/1998 | Musgrave et al. |
| 5,807,350 A | 9/1998 | Diaz |
| 5,813,411 A | 9/1998 | Van Bladel et al. |
| 5,817,058 A | 10/1998 | Shaw |
| 5,817,069 A | 10/1998 | Arnett |
| 5,824,001 A | 10/1998 | Erskine |
| 5,827,202 A | 10/1998 | Miraki et al. |
| 5,827,221 A | 10/1998 | Phelps |
| 5,827,227 A | 10/1998 | DeLago |
| 5,830,190 A | 11/1998 | Howell |
| 5,839,470 A | 11/1998 | Hiejima et al. |
| 5,843,038 A | 12/1998 | Bailey |
| 5,846,259 A | 12/1998 | Berthiaume |
| 5,851,196 A | 12/1998 | Arnett |
| 5,853,393 A | 12/1998 | Bogert |
| 5,855,615 A | 1/1999 | Bley et al. |
| 5,858,002 A | 1/1999 | Jesch |
| 5,865,806 A | 2/1999 | Howell |
| 5,873,864 A | 2/1999 | Luther et al. |
| 5,879,332 A | 3/1999 | Schwemberger et al. |
| 5,885,217 A | 3/1999 | Gisselberg et al. |
| 5,885,251 A | 3/1999 | Luther |
| 5,891,098 A | 4/1999 | Huang |
| 5,891,105 A | 4/1999 | Mahurkar |
| 5,895,398 A | 4/1999 | Wensel et al. |
| 5,902,274 A | 5/1999 | Yamamoto et al. |
| 5,902,832 A | 5/1999 | Van Bladel et al. |
| 5,911,705 A | 6/1999 | Howell |
| 5,911,710 A | 6/1999 | Barry et al. |
| 5,913,848 A | 6/1999 | Luther et al. |
| 5,916,208 A | 6/1999 | Luther et al. |
| 5,928,199 A | 7/1999 | Nakagami |
| 5,935,110 A | 8/1999 | Brimhall |
| 5,941,854 A | 8/1999 | Bhitiyakul |
| 5,944,690 A | 8/1999 | Falwell et al. |
| 5,947,930 A | 9/1999 | Schwemberger et al. |
| 5,951,520 A | 9/1999 | Burzynski et al. |
| 5,954,698 A | 9/1999 | Pike |
| 5,957,893 A | 9/1999 | Luther et al. |
| 5,964,744 A | 10/1999 | Balbierz et al. |
| 5,967,490 A | 10/1999 | Pike |
| 5,984,895 A | 11/1999 | Padilla et al. |
| 5,984,903 A | 11/1999 | Nadal |
| 5,989,220 A | 11/1999 | Shaw et al. |
| 5,989,271 A | 11/1999 | Bonnette et al. |
| 5,997,507 A | 12/1999 | Dysarz |
| 5,997,510 A | 12/1999 | Schwemberger |
| 6,004,278 A | 12/1999 | Botich et al. |
| 6,004,294 A | 12/1999 | Brimhall et al. |
| 6,004,295 A | 12/1999 | Langer et al. |
| 6,011,988 A | 1/2000 | Lynch et al. |
| 6,019,736 A | 2/2000 | Avellanet et al. |

(56) References Cited

U.S. PATENT DOCUMENTS

| | | |
|---|---|---|
| 6,022,319 A | 2/2000 | Willard et al. |
| 6,024,727 A | 2/2000 | Thorne et al. |
| 6,045,734 A | 4/2000 | Luther et al. |
| 6,056,726 A | 5/2000 | Isaacson |
| 6,066,100 A | 5/2000 | Willard et al. |
| 6,074,378 A | 6/2000 | Mouri et al. |
| 6,077,244 A | 6/2000 | Botich et al. |
| 6,080,137 A | 6/2000 | Pike |
| 6,083,237 A | 7/2000 | Huitema et al. |
| 6,096,004 A | 8/2000 | Meglan et al. |
| 6,096,005 A | 8/2000 | Botich et al. |
| 6,126,641 A | 10/2000 | Shields |
| 6,139,532 A | 10/2000 | Howell et al. |
| 6,139,557 A | 10/2000 | Passafaro et al. |
| 6,159,179 A | 12/2000 | Simonson |
| 6,171,234 B1 | 1/2001 | White et al. |
| 6,171,287 B1 | 1/2001 | Lynn et al. |
| 6,176,842 B1 | 1/2001 | Tachibana et al. |
| 6,193,690 B1 | 2/2001 | Dysarz |
| 6,197,001 B1 | 3/2001 | Wilson et al. |
| 6,197,007 B1 | 3/2001 | Thorne et al. |
| 6,197,041 B1 | 3/2001 | Shichman et al. |
| 6,203,527 B1 | 3/2001 | Zadini et al. |
| 6,213,978 B1 | 4/2001 | Voyten |
| 6,217,558 B1 | 4/2001 | Zadini et al. |
| 6,221,047 B1 | 4/2001 | Greene et al. |
| 6,221,049 B1 | 4/2001 | Selmon et al. |
| 6,228,060 B1 | 5/2001 | Howell |
| 6,228,062 B1 | 5/2001 | Howell et al. |
| 6,228,073 B1 | 5/2001 | Noone et al. |
| 6,245,045 B1 | 6/2001 | Stratienko |
| 6,251,092 B1 | 6/2001 | Qin et al. |
| 6,268,399 B1 | 7/2001 | Hultine et al. |
| 6,270,480 B1 | 8/2001 | Dorr et al. |
| 6,273,871 B1 | 8/2001 | Davis et al. |
| 6,280,419 B1 | 8/2001 | Vojtasek |
| 6,309,379 B1 | 10/2001 | Willard et al. |
| 6,319,244 B2 | 11/2001 | Suresh et al. |
| 6,322,537 B1 | 11/2001 | Chang |
| D452,003 S | 12/2001 | Niermann |
| 6,325,781 B1 | 12/2001 | Takagi et al. |
| 6,325,797 B1 | 12/2001 | Stewart et al. |
| 6,336,914 B1 | 1/2002 | Gillespie, III |
| 6,352,520 B1 | 3/2002 | Miyazaki et al. |
| 6,368,337 B1 | 4/2002 | Kieturakis et al. |
| 6,379,333 B1 | 4/2002 | Brimhall et al. |
| 6,379,372 B1 | 4/2002 | Dehdashtian et al. |
| D457,955 S | 5/2002 | Bilitz |
| 6,406,442 B1 | 6/2002 | McFann et al. |
| D460,179 S | 7/2002 | Isoda et al. |
| 6,422,989 B1 | 7/2002 | Hektner |
| 6,436,070 B1 | 8/2002 | Botich et al. |
| 6,436,112 B2 | 8/2002 | Wensel et al. |
| 6,451,052 B1 | 9/2002 | Burmeister et al. |
| 6,461,362 B1 | 10/2002 | Halseth et al. |
| 6,475,217 B1 | 11/2002 | Platt |
| 6,478,779 B1 | 11/2002 | Hu |
| 6,485,473 B1 | 11/2002 | Lynn |
| 6,485,497 B2 | 11/2002 | Wensel et al. |
| 6,497,681 B1 | 12/2002 | Brenner |
| 6,506,181 B2 | 1/2003 | Meng et al. |
| 6,514,236 B1 | 2/2003 | Stratienko |
| 6,524,276 B1 | 2/2003 | Halseth et al. |
| D471,980 S | 3/2003 | Caizza |
| 6,527,759 B1 | 3/2003 | Tachibana et al. |
| 6,530,913 B1 | 3/2003 | Giba et al. |
| 6,530,935 B2 | 3/2003 | Wensel et al. |
| 6,540,725 B1 | 4/2003 | Ponzi |
| 6,540,732 B1 | 4/2003 | Botich et al. |
| 6,544,239 B2 | 4/2003 | Kinsey et al. |
| 6,547,762 B1 | 4/2003 | Botich et al. |
| 6,558,355 B1 | 5/2003 | Metzger et al. |
| 6,582,402 B1 | 6/2003 | Erskine |
| 6,582,440 B1 | 6/2003 | Brumbach |
| 6,585,703 B1 | 7/2003 | Kassel et al. |
| 6,589,262 B1 | 7/2003 | Honebrink et al. |
| 6,595,955 B2 | 7/2003 | Ferguson et al. |
| 6,595,959 B1 | 7/2003 | Stratienko |
| 6,607,511 B2 | 8/2003 | Halseth et al. |
| 6,616,630 B1 | 9/2003 | Woehr et al. |
| 6,620,136 B1 | 9/2003 | Pressly, Sr. et al. |
| 6,623,449 B2 | 9/2003 | Paskar |
| 6,626,868 B1 | 9/2003 | Prestidge et al. |
| 6,626,869 B1 | 9/2003 | Bint |
| 6,632,201 B1 | 10/2003 | Mathias et al. |
| 6,638,252 B2 | 10/2003 | Moulton et al. |
| 6,641,564 B1 | 11/2003 | Kraus |
| 6,645,178 B1 | 11/2003 | Junker et al. |
| 6,652,486 B2 | 11/2003 | Bialecki et al. |
| 6,652,490 B2 | 11/2003 | Howell |
| 6,663,577 B2 | 12/2003 | Jen et al. |
| 6,663,592 B2 | 12/2003 | Rhad et al. |
| 6,666,865 B2 | 12/2003 | Platt |
| 6,679,900 B2 | 1/2004 | Kieturakis et al. |
| 6,689,102 B2 | 2/2004 | Greene |
| 6,692,508 B2 | 2/2004 | Wensel et al. |
| 6,692,509 B2 | 2/2004 | Wensel et al. |
| 6,695,814 B2 | 2/2004 | Greene et al. |
| 6,695,856 B2 | 2/2004 | Kieturakis et al. |
| 6,695,860 B1 | 2/2004 | Ward et al. |
| 6,699,221 B2 | 3/2004 | Vaillancourt |
| 6,702,811 B2 | 3/2004 | Stewart et al. |
| 6,706,018 B2 | 3/2004 | Westlund et al. |
| 6,711,444 B2 | 3/2004 | Koblish |
| 6,712,790 B1 | 3/2004 | Prestidge et al. |
| 6,712,797 B1 | 3/2004 | Southern, Jr. |
| 6,716,197 B2 | 4/2004 | Svendsen |
| 6,730,062 B2 | 5/2004 | Hoffman et al. |
| 6,740,063 B2 | 5/2004 | Lynn |
| 6,740,096 B2 | 5/2004 | Teague et al. |
| 6,745,080 B2 | 6/2004 | Koblish |
| 6,749,588 B1 | 6/2004 | Howell et al. |
| 6,764,468 B1 | 7/2004 | East |
| 6,776,788 B1 | 8/2004 | Klint et al. |
| 6,796,962 B2 | 9/2004 | Ferguson et al. |
| 6,824,545 B2 | 11/2004 | Sepetka et al. |
| 6,832,715 B2 | 12/2004 | Eungard et al. |
| 6,835,190 B2 | 12/2004 | Nguyen |
| 6,837,867 B2 | 1/2005 | Kortelling |
| 6,860,871 B2 | 3/2005 | Kuracina et al. |
| 6,872,193 B2 | 3/2005 | Shaw et al. |
| 6,887,220 B2 | 5/2005 | Hogendijk |
| 6,902,546 B2 | 6/2005 | Ferguson |
| 6,905,483 B2 | 6/2005 | Newby et al. |
| 6,913,595 B2 | 7/2005 | Mastorakis |
| 6,916,311 B2 | 7/2005 | Vojtasek |
| 6,921,386 B2 | 7/2005 | Shue et al. |
| 6,921,391 B1 | 7/2005 | Barker et al. |
| 6,929,624 B1 | 8/2005 | Del Castillo |
| 6,939,325 B2 | 9/2005 | Haining |
| 6,942,652 B1 | 9/2005 | Pressly, Sr. et al. |
| 6,953,448 B2 | 10/2005 | Moulton et al. |
| 6,958,054 B2 | 10/2005 | Fitzgerald |
| 6,958,055 B2 | 10/2005 | Donnan et al. |
| 6,960,191 B2 | 11/2005 | Howlett et al. |
| 6,972,002 B2 | 12/2005 | Thorne |
| 6,974,438 B2 | 12/2005 | Shekalim |
| 6,994,693 B2 | 2/2006 | Tal |
| 7,001,396 B2 | 2/2006 | Glazier et al. |
| 7,004,927 B2 | 2/2006 | Ferguson et al. |
| 7,008,404 B2 | 3/2006 | Nakajima |
| 7,018,372 B2 | 3/2006 | Casey et al. |
| 7,018,390 B2 | 3/2006 | Turovskiy et al. |
| 7,025,746 B2 | 4/2006 | Tal |
| 7,029,467 B2 | 4/2006 | Currier et al. |
| 7,033,335 B2 | 4/2006 | Haarala et al. |
| 7,044,935 B2 | 5/2006 | Shue et al. |
| 7,060,055 B2 | 6/2006 | Wilkinson et al. |
| 7,090,656 B1 | 8/2006 | Botich et al. |
| 7,094,243 B2 | 8/2006 | Mulholland et al. |
| 7,097,633 B2 | 8/2006 | Botich et al. |
| 7,125,396 B2 | 10/2006 | Leinsing et al. |
| 7,141,040 B2 | 11/2006 | Lichtenberg |
| 7,153,276 B2 | 12/2006 | Barker et al. |

(56) References Cited

U.S. PATENT DOCUMENTS

| | | |
|---|---|---|
| 7,163,520 B2 | 1/2007 | Bernard et al. |
| 7,169,159 B2 | 1/2007 | Green et al. |
| 7,179,244 B2 | 2/2007 | Smith et al. |
| 7,191,900 B2 | 3/2007 | Opie et al. |
| 7,192,433 B2 | 3/2007 | Osypka et al. |
| 7,204,813 B2 | 4/2007 | Shue et al. |
| 7,291,130 B2 | 11/2007 | McGurk |
| 7,303,547 B2 | 12/2007 | Pressly, Sr. et al. |
| 7,303,548 B2 | 12/2007 | Rhad et al. |
| 7,314,462 B2 | 1/2008 | O'Reagan et al. |
| 7,331,966 B2 | 2/2008 | Soma et al. |
| 7,344,516 B2 | 3/2008 | Erskine |
| 7,354,422 B2 | 4/2008 | Riesenberger et al. |
| 7,381,205 B2 | 6/2008 | Thommen |
| 7,396,346 B2 | 7/2008 | Nakajima |
| 7,413,562 B2 | 8/2008 | Ferguson et al. |
| 7,422,572 B2 | 9/2008 | Popov et al. |
| 7,458,954 B2 | 12/2008 | Ferguson et al. |
| 7,465,294 B1 | 12/2008 | Vladimirsky |
| 7,468,057 B2 | 12/2008 | Ponzi |
| 7,470,254 B2 | 12/2008 | Basta et al. |
| 7,491,176 B2 | 2/2009 | Mann |
| 7,494,010 B2 | 2/2009 | Opie et al. |
| 7,500,965 B2 | 3/2009 | Menzi et al. |
| 7,507,222 B2 | 3/2009 | Cindrich et al. |
| 7,513,887 B2 | 4/2009 | Halseth et al. |
| 7,513,888 B2 | 4/2009 | Sircom et al. |
| 7,524,306 B2 | 4/2009 | Botich et al. |
| 7,530,965 B2 | 5/2009 | Villa et al. |
| 7,534,227 B2 | 5/2009 | Kulli |
| 7,544,170 B2 | 6/2009 | Williams et al. |
| 7,556,617 B2 | 7/2009 | Voorhees, Jr. et al. |
| 7,566,323 B2 | 7/2009 | Chang |
| D601,243 S | 9/2009 | Bierman et al. |
| 7,597,681 B2 | 10/2009 | Sutton et al. |
| D604,839 S | 11/2009 | Crawford et al. |
| 7,611,485 B2 | 11/2009 | Ferguson |
| 7,618,395 B2 | 11/2009 | Ferguson |
| 7,628,769 B2 | 12/2009 | Grandt et al. |
| 7,632,243 B2 | 12/2009 | Bialecki et al. |
| 7,645,263 B2 | 1/2010 | Angel et al. |
| 7,654,988 B2 | 2/2010 | Moulton et al. |
| 7,658,725 B2 | 2/2010 | Bialecki et al. |
| D612,043 S | 3/2010 | Young et al. |
| 7,678,080 B2 | 3/2010 | Shue et al. |
| 7,691,088 B2 | 4/2010 | Howell |
| 7,691,090 B2 | 4/2010 | Belley et al. |
| 7,691,093 B2 | 4/2010 | Brimhall |
| 7,695,458 B2 | 4/2010 | Belley et al. |
| 7,699,807 B2 | 4/2010 | Faust et al. |
| D615,197 S | 5/2010 | Koh et al. |
| 7,708,721 B2 | 5/2010 | Khaw |
| 7,713,243 B2 | 5/2010 | Hillman |
| 7,717,875 B2 | 5/2010 | Knudson et al. |
| 7,722,567 B2 | 5/2010 | Tal |
| 7,722,569 B2 | 5/2010 | Soderholm et al. |
| D617,893 S | 6/2010 | Bierman et al. |
| 7,731,691 B2 | 6/2010 | Cote et al. |
| 7,736,332 B2 | 6/2010 | Carlyon et al. |
| 7,736,337 B2 | 6/2010 | Diep et al. |
| 7,736,339 B2 | 6/2010 | Woehr et al. |
| 7,736,342 B2 | 6/2010 | Abriles et al. |
| 7,740,615 B2 | 6/2010 | Shaw et al. |
| 7,744,574 B2 | 6/2010 | Pederson et al. |
| 7,753,877 B2 | 7/2010 | Bialecki et al. |
| 7,753,887 B2 | 7/2010 | Botich et al. |
| 7,762,984 B2 | 7/2010 | Kumoyama et al. |
| 7,762,993 B2 | 7/2010 | Perez |
| 7,766,879 B2 | 8/2010 | Tan et al. |
| 7,776,052 B2 | 8/2010 | Greenberg et al. |
| 7,785,296 B2 | 8/2010 | Muskatello et al. |
| 7,794,424 B2 | 9/2010 | Paskar |
| 7,798,994 B2 | 9/2010 | Brimhall |
| 7,803,142 B2 | 9/2010 | Longson et al. |
| 7,828,773 B2 | 11/2010 | Swisher et al. |
| 7,828,774 B2 | 11/2010 | Harding et al. |
| 7,850,644 B2 | 12/2010 | Gonzalez et al. |
| 7,896,862 B2 | 3/2011 | Long et al. |
| 7,905,857 B2 | 3/2011 | Swisher |
| 7,914,488 B2 | 3/2011 | Dickerson |
| 7,914,492 B2 | 3/2011 | Heuser |
| 7,922,696 B2 | 4/2011 | Tal et al. |
| 7,922,698 B2 | 4/2011 | Riesenberger et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 7,972,324 B2 | 7/2011 | Quint |
| 8,029,470 B2 | 10/2011 | Whiting et al. |
| 8,029,472 B2 | 10/2011 | Leinsing et al. |
| 8,048,031 B2 | 11/2011 | Shaw et al. |
| 8,048,039 B2 | 11/2011 | Carlyon et al. |
| 8,057,404 B2 | 11/2011 | Fujiwara et al. |
| 8,079,979 B2 | 12/2011 | Moorehead |
| D653,329 S | 1/2012 | Lee-Sepsick |
| 8,105,286 B2 | 1/2012 | Anderson et al. |
| 8,105,315 B2 | 1/2012 | Johnson et al. |
| 8,123,727 B2 | 2/2012 | Luther et al. |
| 8,152,758 B2 | 4/2012 | Chan et al. |
| 8,162,881 B2 | 4/2012 | Lilley, Jr. et al. |
| 8,167,851 B2 | 5/2012 | Sen |
| 8,177,753 B2 | 5/2012 | Vitullo et al. |
| RE43,473 E | 6/2012 | Newby et al. |
| 8,192,402 B2 | 6/2012 | Anderson et al. |
| 8,202,253 B1 | 6/2012 | Wexler |
| 8,206,343 B2 | 6/2012 | Racz |
| 8,221,387 B2 | 7/2012 | Shelso et al. |
| 8,251,923 B2 | 8/2012 | Carrez et al. |
| 8,251,950 B2 | 8/2012 | Albert et al. |
| D667,111 S | 9/2012 | Robinson |
| 8,257,322 B2 | 9/2012 | Koehler et al. |
| 8,273,054 B2 | 9/2012 | St. Germain et al. |
| 8,286,657 B2 | 10/2012 | Belley et al. |
| 8,298,186 B2 | 10/2012 | Popov |
| 8,308,691 B2 | 11/2012 | Woehr et al. |
| D672,456 S | 12/2012 | Lee-Sepsick |
| 8,328,762 B2 | 12/2012 | Woehr et al. |
| 8,328,837 B2 | 12/2012 | Binmoeller |
| 8,333,735 B2 | 12/2012 | Woehr et al. |
| 8,337,463 B2 | 12/2012 | Woehr et al. |
| 8,337,471 B2 | 12/2012 | Baid |
| D675,318 S | 1/2013 | Luk et al. |
| 8,361,020 B2 | 1/2013 | Stout |
| 8,377,006 B2 | 2/2013 | Tal et al. |
| 8,388,583 B2 | 3/2013 | Stout et al. |
| 8,403,886 B2 | 3/2013 | Bialecki et al. |
| 8,412,300 B2 | 4/2013 | Sonderegger |
| 8,419,688 B2 | 4/2013 | Woehr et al. |
| 8,454,536 B2 | 6/2013 | Raulerson et al. |
| 8,460,247 B2 | 6/2013 | Woehr et al. |
| 8,469,928 B2 | 6/2013 | Stout et al. |
| 8,496,628 B2 | 7/2013 | Erskine |
| 8,506,533 B2 | 8/2013 | Carlyon et al. |
| 8,509,340 B2 | 8/2013 | Michelitsch |
| 8,517,959 B2 | 8/2013 | Kurosawa et al. |
| 8,535,271 B2 | 9/2013 | Fuchs et al. |
| 8,540,728 B2 | 9/2013 | Woehr et al. |
| 8,574,203 B2 | 11/2013 | Stout et al. |
| 8,585,660 B2 | 11/2013 | Murphy |
| 8,591,467 B2 | 11/2013 | Walker et al. |
| 8,591,468 B2 | 11/2013 | Woehr et al. |
| 8,597,249 B2 | 12/2013 | Woehr et al. |
| 8,622,931 B2 | 1/2014 | Teague et al. |
| 8,622,972 B2 | 1/2014 | Nystrom et al. |
| 8,647,301 B2 | 2/2014 | Bialecki et al. |
| 8,647,313 B2 | 2/2014 | Woehr et al. |
| 8,647,324 B2 | 2/2014 | Delegge et al. |
| 8,652,104 B2 | 2/2014 | Goral et al. |
| 8,657,790 B2 | 2/2014 | Tal et al. |
| 8,672,888 B2 | 3/2014 | Tal |
| 8,679,063 B2 | 3/2014 | Stout et al. |
| 8,690,833 B2 | 4/2014 | Belson |
| 8,721,546 B2 | 5/2014 | Belson |
| 8,728,030 B2 | 5/2014 | Woehr |
| 8,728,035 B2 | 5/2014 | Warring et al. |

(56) References Cited

U.S. PATENT DOCUMENTS

| | | |
|---|---|---|
| 8,740,964 B2 | 6/2014 | Hartley |
| 8,747,387 B2 | 6/2014 | Belley et al. |
| 8,753,317 B2 | 6/2014 | Osborne et al. |
| 8,764,711 B2 | 7/2014 | Kuracina et al. |
| D710,495 S | 8/2014 | Wu et al. |
| 8,814,833 B2 | 8/2014 | Farrell et al. |
| D713,957 S | 9/2014 | Woehr et al. |
| 8,845,584 B2 | 9/2014 | Ferguson et al. |
| 8,864,714 B2 | 10/2014 | Harding et al. |
| 8,900,192 B2 | 12/2014 | Anderson et al. |
| 8,932,257 B2 | 1/2015 | Woehr |
| 8,932,258 B2 | 1/2015 | Blanchard et al. |
| 8,956,327 B2 | 2/2015 | Bierman et al. |
| 8,974,426 B2 | 3/2015 | Corcoran et al. |
| 8,979,802 B2 | 3/2015 | Woehr |
| 8,986,227 B2 | 3/2015 | Belson |
| 8,998,852 B2 | 4/2015 | Blanchard et al. |
| 9,005,169 B2 | 4/2015 | Gravesen et al. |
| 9,011,351 B2 | 4/2015 | Hoshinouchi |
| 9,011,381 B2 | 4/2015 | Yamada et al. |
| 9,033,927 B2 | 5/2015 | Maan et al. |
| D733,289 S | 6/2015 | Blanchard et al. |
| 9,044,583 B2 | 6/2015 | Vaillancourt |
| D735,321 S | 7/2015 | Blanchard |
| 9,095,683 B2 | 8/2015 | Hall et al. |
| 9,101,746 B2 | 8/2015 | Stout et al. |
| 9,114,241 B2 | 8/2015 | Stout et al. |
| 9,138,252 B2 | 9/2015 | Bierman et al. |
| 9,138,545 B2 | 9/2015 | Shaw et al. |
| 9,138,559 B2 | 9/2015 | Odland et al. |
| RE45,776 E | 10/2015 | Root et al. |
| 9,162,036 B2 | 10/2015 | Caples et al. |
| 9,162,037 B2 | 10/2015 | Belson et al. |
| 9,180,275 B2 | 11/2015 | Helm |
| 9,216,109 B2 | 12/2015 | Badawi et al. |
| 9,220,531 B2 | 12/2015 | Datta et al. |
| 9,220,871 B2 | 12/2015 | Thorne et al. |
| 2001/0014786 A1 | 8/2001 | Greene et al. |
| 2001/0020153 A1 | 9/2001 | Howell |
| 2002/0077595 A1 | 6/2002 | Hundertmark et al. |
| 2002/0107526 A1 | 8/2002 | Greenberg et al. |
| 2002/0128604 A1 | 9/2002 | Nakajima |
| 2002/0165497 A1 | 11/2002 | Greene |
| 2002/0177812 A1 | 11/2002 | Moulton et al. |
| 2003/0032922 A1 | 2/2003 | Moorehead |
| 2003/0060760 A1 | 3/2003 | Botich et al. |
| 2003/0073956 A1 | 4/2003 | Hoffman et al. |
| 2003/0120214 A1 | 6/2003 | Howell |
| 2003/0153874 A1 | 8/2003 | Tal |
| 2003/0187396 A1 | 10/2003 | Ponzi |
| 2003/0204186 A1 | 10/2003 | Geistert |
| 2004/0019329 A1 | 1/2004 | Erskine |
| 2004/0044302 A1 | 3/2004 | Bernard et al. |
| 2004/0044313 A1 | 3/2004 | Nakajima |
| 2004/0092879 A1 | 5/2004 | Kraus et al. |
| 2004/0106903 A1 | 6/2004 | Shue et al. |
| 2004/0111059 A1 | 6/2004 | Howlett et al. |
| 2004/0122373 A1 | 6/2004 | Botich et al. |
| 2004/0193118 A1 | 9/2004 | Bergeron |
| 2004/0236288 A1 | 11/2004 | Howell et al. |
| 2004/0243061 A1 | 12/2004 | McGurk |
| 2004/0267204 A1 | 12/2004 | Brustowicz |
| 2005/0004524 A1 | 1/2005 | Newby et al. |
| 2005/0010095 A1 | 1/2005 | Stewart et al. |
| 2005/0020940 A1 | 1/2005 | Opie et al. |
| 2005/0027256 A1 | 2/2005 | Barker et al. |
| 2005/0033137 A1 | 2/2005 | Oral et al. |
| 2005/0040061 A1 | 2/2005 | Opie et al. |
| 2005/0075606 A1 | 4/2005 | Botich et al. |
| 2005/0107769 A1 | 5/2005 | Thommen |
| 2005/0119619 A1 | 6/2005 | Haining |
| 2005/0131350 A1 | 6/2005 | Shaw et al. |
| 2005/0165355 A1 | 7/2005 | Fitzgerald |
| 2005/0197623 A1 | 9/2005 | Leeflang et al. |
| 2005/0245847 A1 | 11/2005 | Schaeffer |
| 2005/0256505 A1 | 11/2005 | Long et al. |
| 2005/0273057 A1 | 12/2005 | Popov |
| 2006/0025721 A1 | 2/2006 | Duffy et al. |
| 2006/0079787 A1 | 4/2006 | Whiting et al. |
| 2006/0084964 A1 | 4/2006 | Knudson et al. |
| 2006/0155245 A1 | 7/2006 | Woehr |
| 2006/0167405 A1 | 7/2006 | King et al. |
| 2006/0229563 A1 | 10/2006 | O'Reagan et al. |
| 2006/0264834 A1 | 11/2006 | Vaillancourt |
| 2007/0043422 A1 | 2/2007 | Shmulewitz et al. |
| 2007/0060999 A1 | 3/2007 | Randall et al. |
| 2007/0083162 A1 | 4/2007 | O'Reagan et al. |
| 2007/0083188 A1 | 4/2007 | Grandt et al. |
| 2007/0100284 A1 | 5/2007 | Leinsing et al. |
| 2007/0123803 A1 | 5/2007 | Fujiwara et al. |
| 2007/0142779 A1 | 6/2007 | Duane et al. |
| 2007/0179446 A1 | 8/2007 | Carrez et al. |
| 2007/0191777 A1 | 8/2007 | King |
| 2007/0193903 A1 | 8/2007 | Opie et al. |
| 2007/0225647 A1 | 9/2007 | Luther et al. |
| 2007/0244438 A1 | 10/2007 | Perez |
| 2007/0276288 A1 | 11/2007 | Khaw |
| 2008/0097330 A1 | 4/2008 | King et al. |
| 2008/0108911 A1 | 5/2008 | Palmer |
| 2008/0108944 A1 | 5/2008 | Woehr et al. |
| 2008/0108974 A1 | 5/2008 | Yee Roth |
| 2008/0125709 A1 | 5/2008 | Chang et al. |
| 2008/0131300 A1 | 6/2008 | Junod et al. |
| 2008/0243165 A1 | 10/2008 | Mauch et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0300574 A1 | 12/2008 | Belson et al. |
| 2009/0030380 A1 | 1/2009 | Binmoeller |
| 2009/0036836 A1 | 2/2009 | Nystrom et al. |
| 2009/0048566 A1 | 2/2009 | Ferguson et al. |
| 2009/0131872 A1 | 5/2009 | Popov |
| 2009/0157006 A1 | 6/2009 | Nardeo et al. |
| 2009/0221961 A1 | 9/2009 | Tal et al. |
| 2009/0292243 A1 | 11/2009 | Harding et al. |
| 2009/0299291 A1 | 12/2009 | Baid |
| 2010/0010447 A1 | 1/2010 | Luther et al. |
| 2010/0036331 A1 | 2/2010 | Sen |
| 2010/0087787 A1 | 4/2010 | Woehr et al. |
| 2010/0094310 A1 | 4/2010 | Warring et al. |
| 2010/0168674 A1 | 7/2010 | Shaw et al. |
| 2010/0204654 A1 | 8/2010 | Mulholland et al. |
| 2010/0204675 A1 | 8/2010 | Woehr et al. |
| 2010/0210934 A1 | 8/2010 | Belson |
| 2010/0246707 A1 | 9/2010 | Michelitsch |
| 2010/0331732 A1 | 12/2010 | Raulerson et al. |
| 2011/0009827 A1 | 1/2011 | Bierman et al. |
| 2011/0015573 A1 | 1/2011 | Maan et al. |
| 2011/0021994 A1 | 1/2011 | Anderson et al. |
| 2011/0125097 A1 | 5/2011 | Shaw et al. |
| 2011/0137252 A1 | 6/2011 | Oster et al. |
| 2011/0196315 A1 | 8/2011 | Chappel |
| 2011/0207157 A1 | 8/2011 | Gautier et al. |
| 2011/0218496 A1 | 9/2011 | Bierman |
| 2011/0251559 A1 | 10/2011 | Tal et al. |
| 2011/0276002 A1 | 11/2011 | Bierman |
| 2011/0282285 A1 | 11/2011 | Blanchard et al. |
| 2011/0288482 A1 | 11/2011 | Farrell et al. |
| 2011/0306933 A1 | 12/2011 | Djordjevic et al. |
| 2011/0319838 A1 | 12/2011 | Goral et al. |
| 2012/0053523 A1 | 3/2012 | Harding |
| 2012/0078231 A1 | 3/2012 | Hoshinouchi |
| 2012/0123332 A1 | 5/2012 | Erskine |
| 2012/0157854 A1 | 6/2012 | Kurrus et al. |
| 2012/0184896 A1 | 7/2012 | DeLegge et al. |
| 2012/0197200 A1 | 8/2012 | Belson |
| 2012/0220942 A1 | 8/2012 | Hall et al. |
| 2012/0220956 A1 | 8/2012 | Kuracina et al. |
| 2012/0259293 A1 | 10/2012 | Bialecki et al. |
| 2012/0271232 A1 | 10/2012 | Katsurada et al. |
| 2012/0296282 A1 | 11/2012 | Koehler et al. |
| 2012/0316500 A1 | 12/2012 | Bierman et al. |
| 2012/0323181 A1 | 12/2012 | Shaw et al. |
| 2013/0204206 A1 | 8/2013 | Morgan et al. |

(56) References Cited

U.S. PATENT DOCUMENTS

| | | |
|---|---|---|
| 2013/0204226 A1 | 8/2013 | Keyser |
| 2013/0218082 A1 | 8/2013 | Hyer et al. |
| 2013/0304030 A1 | 11/2013 | Gray et al. |
| 2013/0324930 A1 | 12/2013 | Fuchs et al. |
| 2014/0012203 A1 | 1/2014 | Woehr et al. |
| 2014/0031752 A1 | 1/2014 | Blanchard et al. |
| 2014/0039461 A1 | 2/2014 | Anderson et al. |
| 2014/0058357 A1 | 2/2014 | Keyser et al. |
| 2014/0073928 A1 | 3/2014 | Yamashita et al. |
| 2014/0074034 A1 | 3/2014 | Tanabe et al. |
| 2014/0088509 A1 | 3/2014 | Sonderegger et al. |
| 2014/0094774 A1 | 4/2014 | Blanchard |
| 2014/0094836 A1 | 4/2014 | Feng et al. |
| 2014/0114239 A1 | 4/2014 | Dib et al. |
| 2014/0128775 A1 | 5/2014 | Andreae et al. |
| 2014/0135702 A1 | 5/2014 | Woehr et al. |
| 2014/0135703 A1 | 5/2014 | Yeh et al. |
| 2014/0180250 A1 | 6/2014 | Belson |
| 2014/0188003 A1 | 7/2014 | Belson |
| 2014/0194853 A1 | 7/2014 | Morgan et al. |
| 2014/0214005 A1 | 7/2014 | Belson |
| 2014/0221977 A1 | 8/2014 | Belson |
| 2014/0249488 A1 | 9/2014 | Woehr |
| 2014/0257359 A1 | 9/2014 | Tegels et al. |
| 2014/0276224 A1 | 9/2014 | Ranganathan et al. |
| 2014/0276434 A1 | 9/2014 | Woehr et al. |
| 2014/0336582 A1 | 11/2014 | Tisci et al. |
| 2014/0357983 A1 | 12/2014 | Toomey et al. |
| 2014/0364809 A1 | 12/2014 | Isaacson et al. |
| 2014/0371715 A1 | 12/2014 | Farrell et al. |
| 2014/0378867 A1 | 12/2014 | Belson |
| 2015/0025467 A1 | 1/2015 | Woehr |
| 2015/0038909 A1 | 2/2015 | Christensen et al. |
| 2015/0038910 A1 | 2/2015 | Harding et al. |
| 2015/0038943 A1 | 2/2015 | Warring et al. |
| 2015/0051584 A1 | 2/2015 | Korkuch et al. |
| 2015/0080801 A1 | 3/2015 | Tanabe et al. |
| 2015/0080810 A1 | 3/2015 | Henderson et al. |
| 2015/0088095 A1 | 3/2015 | Luther et al. |
| 2015/0119806 A1 | 4/2015 | Blanchard et al. |
| 2015/0119852 A1 | 4/2015 | Wexler |
| 2015/0126932 A1 | 5/2015 | Knutsson |
| 2015/0190168 A1 | 7/2015 | Bierman et al. |
| 2015/0190617 A1 | 7/2015 | Anderson et al. |
| 2015/0202414 A1 | 7/2015 | Hwang |
| 2015/0224267 A1 | 8/2015 | Farrell et al. |
| 2015/0231364 A1 | 8/2015 | Blanchard et al. |
| 2015/0290431 A1 | 10/2015 | Hall et al. |
| 2015/0306347 A1 | 10/2015 | Yagi |
| 2015/0306356 A1 | 10/2015 | Gill |
| 2015/0328434 A1 | 11/2015 | Gaur |
| 2015/0328438 A1 | 11/2015 | Baid |
| 2015/0359473 A1 | 12/2015 | Garrett et al. |
| 2016/0015943 A1 | 1/2016 | Belson et al. |
| 2016/0015945 A1 | 1/2016 | Warring et al. |
| 2016/0022963 A1 | 1/2016 | Belson |
| 2016/0256667 A1 | 9/2016 | Ribelin et al. |

FOREIGN PATENT DOCUMENTS

| | | | |
|---|---|---|---|
| CN | 1319023 A | | 10/2001 |
| CN | 102939129 A | | 2/2013 |
| DE | 20210394 U1 | | 9/2002 |
| EP | 417764 A1 | | 3/1991 |
| EP | 475857 A1 | | 3/1992 |
| EP | 515710 A1 | | 12/1992 |
| EP | 567321 A2 | | 10/1993 |
| EP | 652020 A2 | | 5/1995 |
| EP | 747075 A2 | | 12/1996 |
| EP | 750916 A2 | | 1/1997 |
| EP | 778043 A1 | | 6/1997 |
| EP | 800790 A2 | | 10/1997 |
| EP | 832663 A2 | | 4/1998 |
| EP | 910988 A1 | | 4/1999 |
| EP | 942761 A1 | | 9/1999 |
| EP | 1075850 A2 | | 2/2001 |
| EP | 1378263 A2 | | 1/2004 |
| EP | 1418971 A2 | | 5/2004 |
| EP | 1457229 A1 | | 9/2004 |
| EP | 1611916 A1 | | 1/2006 |
| EP | 1907042 A2 | | 4/2008 |
| EP | 2150304 A2 | | 2/2010 |
| EP | 2272432 A1 | | 1/2011 |
| EP | 2569046 A1 | | 3/2013 |
| JP | 2003-159334 A | | 6/2003 |
| JP | 2004-130074 A | | 4/2004 |
| JP | 2004-223252 A | | 8/2004 |
| JP | 2005-137888 A | | 6/2005 |
| JP | 2010-088521 A | | 4/2010 |
| JP | 2013-529111 | | 7/2013 |
| WO | 83/01575 A1 | | 5/1983 |
| WO | 8301575 A1 | | 5/1983 |
| WO | 9213584 A1 | | 8/1992 |
| WO | 92/22344 A1 | | 12/1992 |
| WO | 9222344 A1 | | 12/1992 |
| WO | 9511710 A1 | | 5/1995 |
| WO | 95/19193 A1 | | 7/1995 |
| WO | 9519193 A1 | | 7/1995 |
| WO | 95/23003 A1 | | 8/1995 |
| WO | 9523003 A1 | | 8/1995 |
| WO | 96/32981 A1 | | 10/1996 |
| WO | 9632981 A1 | | 10/1996 |
| WO | 9640359 A1 | | 12/1996 |
| WO | 97/05912 A2 | | 2/1997 |
| WO | 9705912 A2 | | 2/1997 |
| WO | 97/21458 A1 | | 6/1997 |
| WO | 9721458 A1 | | 6/1997 |
| WO | 9745151 A1 | | 12/1997 |
| WO | 98/24494 A1 | | 6/1998 |
| WO | 9824494 A1 | | 6/1998 |
| WO | 9830268 A1 | | 7/1998 |
| WO | 9853875 A1 | | 12/1998 |
| WO | 9908742 A1 | | 2/1999 |
| WO | 9926682 A1 | | 6/1999 |
| WO | 00/06226 A1 | | 2/2000 |
| WO | 00/12160 A1 | | 3/2000 |
| WO | 0012167 A1 | | 3/2000 |
| WO | 00/47256 A1 | | 8/2000 |
| WO | 0107103 A1 | | 2/2001 |
| WO | 0241932 A2 | | 5/2002 |
| WO | 02/066093 A2 | | 8/2002 |
| WO | 03/011381 A1 | | 2/2003 |
| WO | 03/043686 A1 | | 5/2003 |
| WO | 03/047675 A2 | | 6/2003 |
| WO | 2004/018031 A2 | | 3/2004 |
| WO | 2004106203 A3 | | 12/2004 |
| WO | 2005002659 A1 | | 1/2005 |
| WO | 2005/074412 A2 | | 8/2005 |
| WO | 2005/087306 A1 | | 9/2005 |
| WO | 2006062996 A2 | | 6/2006 |
| WO | 2007006055 A2 | | 1/2007 |
| WO | 2007/032343 A1 | | 3/2007 |
| WO | 2007094841 A1 | | 8/2007 |
| WO | 2007/098355 A1 | | 8/2007 |
| WO | 2007098359 A1 | | 8/2007 |
| WO | 2008005618 A2 | | 1/2008 |
| WO | 2008030999 A2 | | 3/2008 |
| WO | 2008/131300 A2 | | 10/2008 |
| WO | 2008137956 A2 | | 11/2008 |
| WO | 2009/001309 A1 | | 12/2008 |
| WO | 2008147600 A1 | | 12/2008 |
| WO | 2009031161 A1 | | 3/2009 |
| WO | 2009114837 A2 | | 9/2009 |
| WO | 2009/124990 A1 | | 10/2009 |
| WO | 2010015676 A1 | | 2/2010 |
| WO | 2010/048449 A2 | | 4/2010 |
| WO | 2010/132608 A2 | | 11/2010 |
| WO | 2011036574 A1 | | 3/2011 |
| WO | 2011143621 A1 | | 11/2011 |
| WO | 2012106266 A1 | | 8/2012 |
| WO | 2012154277 A1 | | 11/2012 |
| WO | 2012174109 A1 | | 12/2012 |
| WO | 2013119557 A1 | | 8/2013 |
| WO | 2013126446 A1 | | 8/2013 |

(56) References Cited

FOREIGN PATENT DOCUMENTS

| WO | 2013187827 | A1 | 12/2013 |
|---|---|---|---|
| WO | 2014006403 | A1 | 1/2014 |
| WO | 2014029424 | A1 | 2/2014 |
| WO | 2014074417 | A2 | 5/2014 |
| WO | 2014081942 | A1 | 5/2014 |
| WO | 2014133617 | A1 | 9/2014 |
| WO | 2014165783 | A1 | 10/2014 |
| WO | 2015035393 | A1 | 3/2015 |
| WO | 2015108913 | A1 | 7/2015 |
| WO | 2015/168655 | A2 | 11/2015 |
| WO | 2015164912 | A1 | 11/2015 |
| WO | 2016/037127 | A1 | 3/2016 |

OTHER PUBLICATIONS

Access Scientific, The PICC Wand® Product Data Sheet, Revision F, May 22, 2012.
BD Angiocath™ Autoguard™ Shielded IV Catheter Brochure, © 2001.
BD Saf-T-Intima™ Integrated Safety IV Catheter Brochure, © 2001.
Becton Dickinson, Insyte® AutoGuard™ Shielded I.V. Catheter Brochure, 1998.
CN 201180029526.7 filed Dec. 14, 2012 First Office Action dated Apr. 21, 2014.
CN 2012800008866.6 filed Aug. 14, 2013 First Office Action dated Dec. 31, 2014.
CN 2012800008866.6 filed Aug. 14, 2013 Second Office Action dated Aug. 17, 2015.
European search report and opinion dated Dec. 1, 2010 for EP Application No. 10075422.5.
Hadaway, Lynn C., A Midline Alternative to Central and Peripheral Venous Access, Caring Magazine, May 1990, pp. 45-50.
International search report and written opinion dated Jan. 16, 2009 for PCT/US2008/062954.
JP 2013-510353 filed Oct. 31, 2012 First Office Action dated Feb. 19, 2015.
Menlo Care, Landmark™ Aquavene® Catheters Brochure, 1992.
Menlo Care, Landmark® Midline Catheters Brochure, 1991.
Menlo Care, Publications on Aquavene® Technology, Aug. 1992.
Notice of allowance dated Jan. 16, 2014 for U.S. Appl. No. 12/598,053.
Notice of allowance dated Feb. 17, 2015 for U.S. Appl. No. 14/477,717.
Office action dated May 8, 2013 for U.S. Appl. No. 12/598,053.
Office action dated Aug. 28, 2013 for U.S. Appl. No. 12/598,053.
Office action dated Oct. 24, 2013 for U.S. Appl. No. 12/598,053.
Office action dated Dec. 4, 2012 for U.S. Appl. No. 12/598,053.
Office action dated Dec. 18, 2014 for U.S. Appl. No. 14/477,717.
PCT/US2011/036530 filed May 13, 2011 International Search Report dated Oct. 6, 2011.
PCT/US2011/036530 filed May 13, 2011 Written Opinion of the International Searching Authority dated Oct. 6, 2011.
PCT/US2012/026618 International Preliminary Report on Patentability dated Aug. 27, 2013.
PCT/US2012/026618 International Search Report and Written Opinion dated Jun. 25, 2012.
PCT/US2013/073577 filed Dec. 6, 2013 International Search Report and Written Opinion dated Feb. 24, 2014.
PR Newswire, Luther Medical Products, Inc. Receives Approval to Supply Improved Neonatal Product to Japan, Aug. 20, 1998.
Rasor, Julia S, Review of Catheter-related infection rates: comparison of conventional catheter materials with Aquavene®, JVAN vol. 1, No. 3, Spring 1991.
U.S. Appl. No. 13/107,781, filed May 13, 2011 Final Office Action dated Jul. 18, 2014.
U.S. Appl. No. 13/107,781, filed May 13, 2011 Non-Final Office Action dated Dec. 30, 2013.
U.S. Appl. No. 13/405,096, filed Feb. 24, 2012 Advisory Action dated Apr. 18, 2014.
U.S. Appl. No. 13/405,096, filed Feb. 24, 2012 Final Office Action dated Jan. 31, 2014.
U.S. Appl. No. 13/405,096, filed Feb. 24, 2012 Non-Final Office Action dated Aug. 20, 2013.
U.S. Appl. No. 13/405,096, filed Feb. 24, 2012 Non-Final Office Action dated Nov. 18, 2014.
U.S. Appl. No. 13/405,096, filed Feb. 24, 2012 Notice of Allowance dated Mar. 11, 2015.
U.S. Appl. No. 14/044,623, filed Oct. 2, 2013 Notice of Allowance dated Nov. 6, 2014.
Waltimire, B. and Rasor, J.S., Midline catheter: Virtually bloodless insertion technique and needle safety tube minimize potential for transmission of bloodborne disease. Sponsored by national Foundation for Infectious Diseases. 5th National forum on AIDS, Hepatitis, and other blood-borne diseases. Atlanta, GA, Mar. 1992.
Access Scientific, The Powerwand® Extended Dwell Catheter Brochure (http://accessscientific.com/media/4Fr-POWERWAND-Brochure.pdf) last accessed Sep. 25, 2015.
BD Medical Systems, I.V. Catheter Family Brochure (2006).
Menlo Care, Landmark® Midline Catheter Maintenance and Reference Guide (1993).
Menlo Care, Landmark® Venous Access Device Insertion Instructions (1992).
U.S. Appl. No. 14/099,050, filed Dec. 6, 2013 Non-Final Office Action dated Dec. 22, 2015.
U.S. Appl. No. 14/174,071, filed Feb. 6, 2014 Restriction Requirement dated Dec. 7, 2014.
U.S. Appl. No. 14/585,800, filed Dec. 30, 2014 Non-Final Office Action dated Oct. 8, 2015.
CN 201280008866.6 filed Aug. 14, 2013 Third Office Action dated Jan. 25, 2016.
Cook Medical "Lunderquist Extra-Stiff wire guide" (2012).
Endovascular Today "Coiled Stainless Steel Guidewires" Buyer's Guide pp. 13-20, (2012).
EP 12782187.4 filed Sep. 10, 2013 European search report and written opinion dated Dec. 17, 2015.
European office action dated Apr. 21, 2008 for EP Application No. 06800027.2.
European office action dated Aug. 6, 2012 for EP Application No. 07783404.2.
European office action dated Oct. 5, 2010 for EP Application No. 07783404.2.
European search report and opinion dated Jul. 10, 2009 for EP Application No. 07783404.2.
International search report and written opinion dated Apr. 2, 2012 for PCT/US2012/023192.
International search report and written opinion dated Jun. 1, 2007 for PCT/US2006/026671.
International search report and written opinion dated Oct. 23, 2008 for PCT/US2007/068393.
JP 2013-510353 filed Oct. 31, 2012 Second Office Action dated Jan. 28, 2016.
Notice of allowance dated Jan. 29, 2014 for U.S. Appl. No. 12/307,519.
Notice of allowance dated Jun. 10, 2015 for U.S. Appl. No. 11/577,491.
Office action dated Mar. 10, 2011 for U.S. Appl. No. 12/307,519.
Office action dated Mar. 15, 2011 for U.S. Appl. No. 11/577,491.
Office action dated Mar. 27, 2013 for U.S. Appl. No. 13/358,099.
Office action dated Aug. 21, 2010 for U.S. Appl. No. 11/577,491.
Office action dated Aug. 18, 2014 for U.S. Appl. No. 11/577,491.
Office action dated Oct. 25, 2010 for U.S. Appl. No. 12/307,519.
Office action dated Nov. 4, 2013 for U.S. Appl. No. 12/307,519.
Office action dated Mar. 12, 2015 for U.S. Appl. No. 11/577,491.
PCT/US15/28950 filed May 1, 2015 International Search Report and Written Opinion dated Oct. 19, 2015.
PCT/US2015/048676 filed Sep. 4, 2015 International search report and written opinion dated Dec. 4, 2015.
U.S. Appl. No. 14/585,800, filed Dec. 30, 2014 Non-Final Office Action dated May 16, 2016.

(56) References Cited

OTHER PUBLICATIONS

U.S. Appl. No. 14/866,441, filed Sep. 25, 2015 Non-Final Office Action dated Mar. 14, 2016.
U.S. Appl. No. 14/174,071, filed Feb. 6, 2014 Non-Final Office Action dated Mar. 31, 2016.
EP 12782187.4 filed Sep. 10, 2013 European search report and written opinion dated Aug. 30, 2016.
EP 138766662 filed Sep. 7, 2015 Extended European Search Report dated Sep. 20, 2016.
JP 2016-107046 filed May 30, 2016 Office Action dated Jul. 28, 2016.
U.S. Appl. No. 14/099,050, filed Dec. 6, 2013 Non-Final Office Action dated Jul. 19, 2016.
U.S. Appl. No. 14/174,071, filed Feb. 6, 2014 Non-Final Office Action dated Jul. 29, 2016.
U.S. Appl. No. 14/192,541, filed Feb. 27, 2014 Non-Final Office Action dated Jul. 20, 2016.

\* cited by examiner

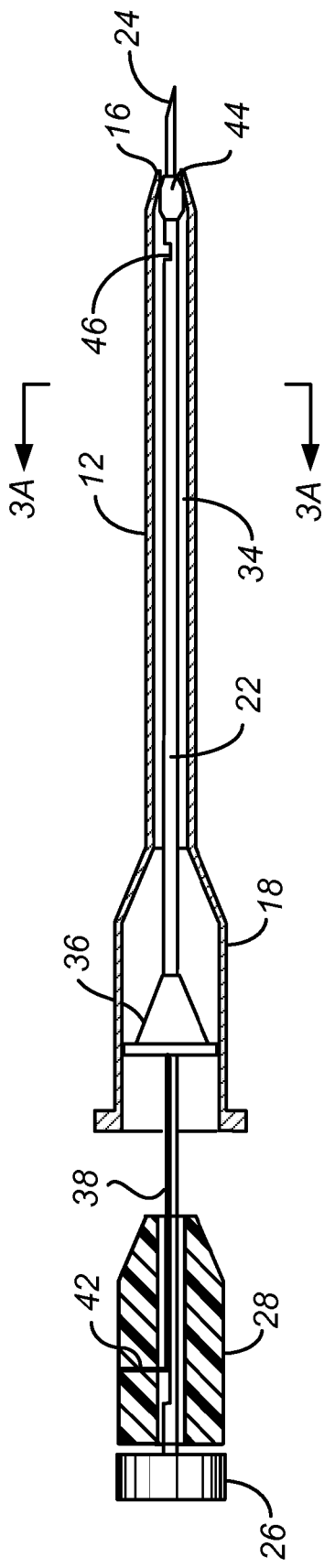
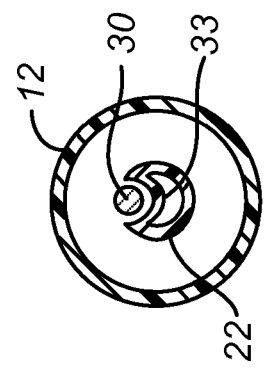
FIG. 3
FIG. 3A
FIG. 3B

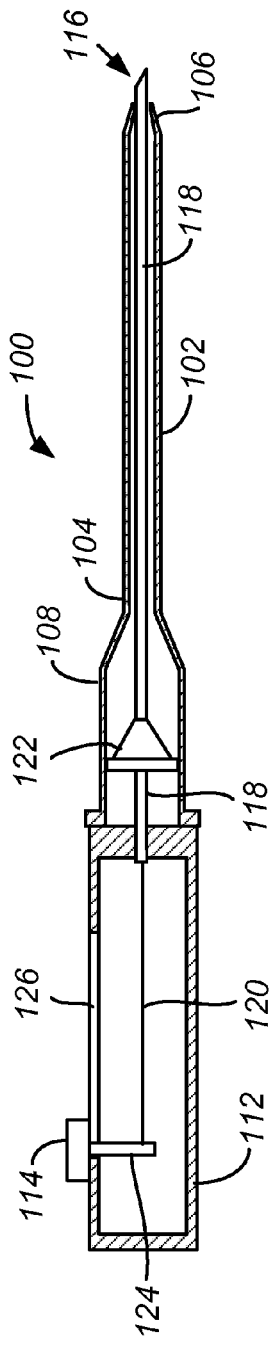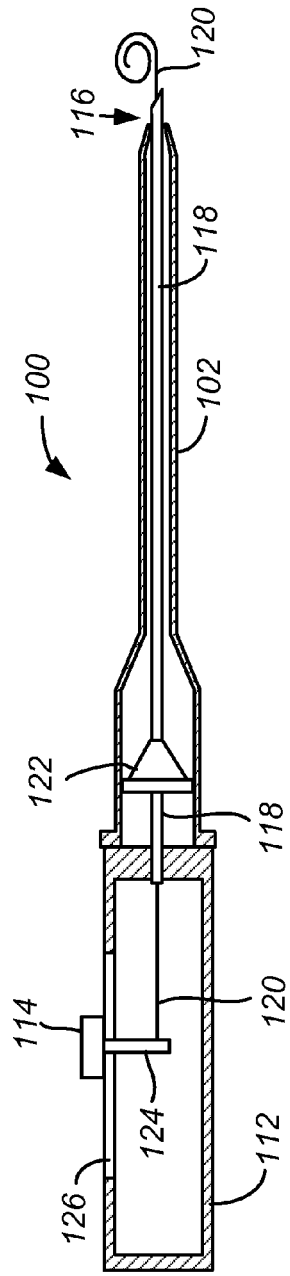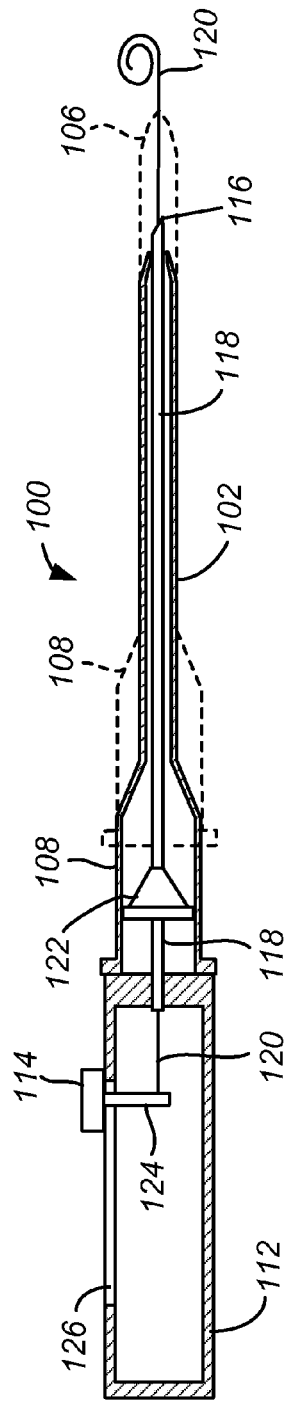

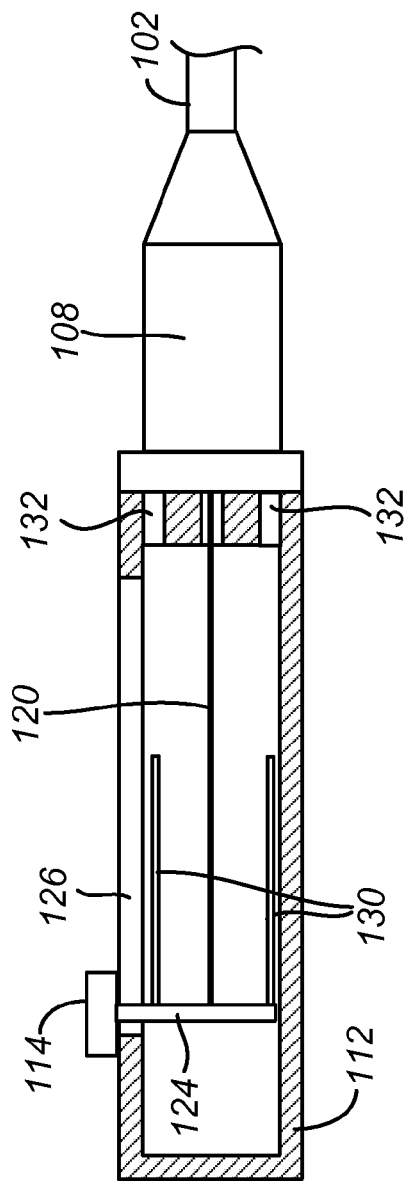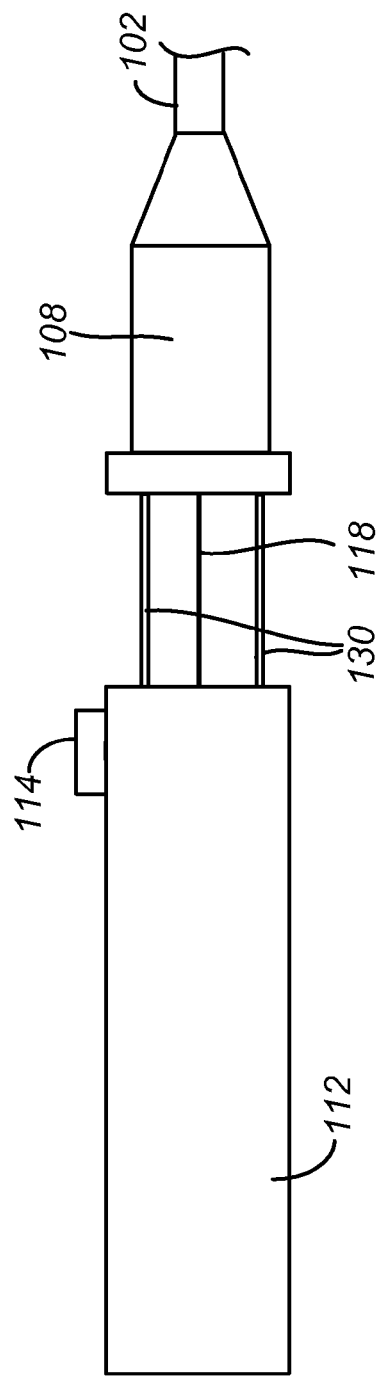
FIG. 7A
FIG. 7B

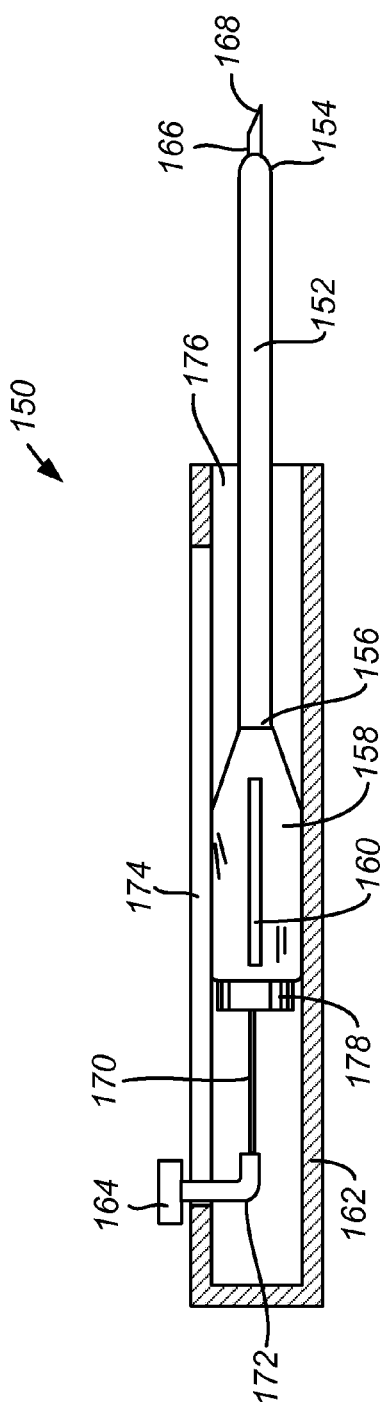
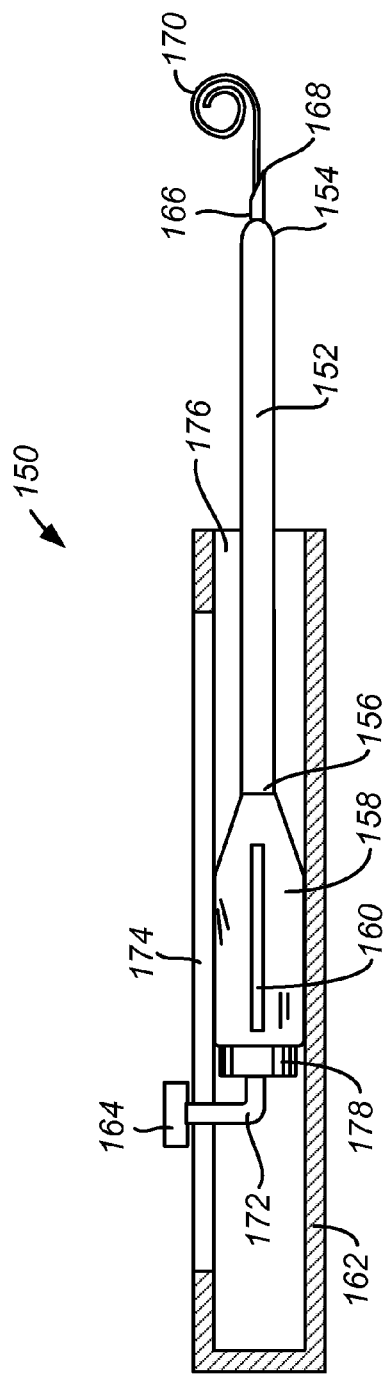
FIG. 9A
FIG. 9B

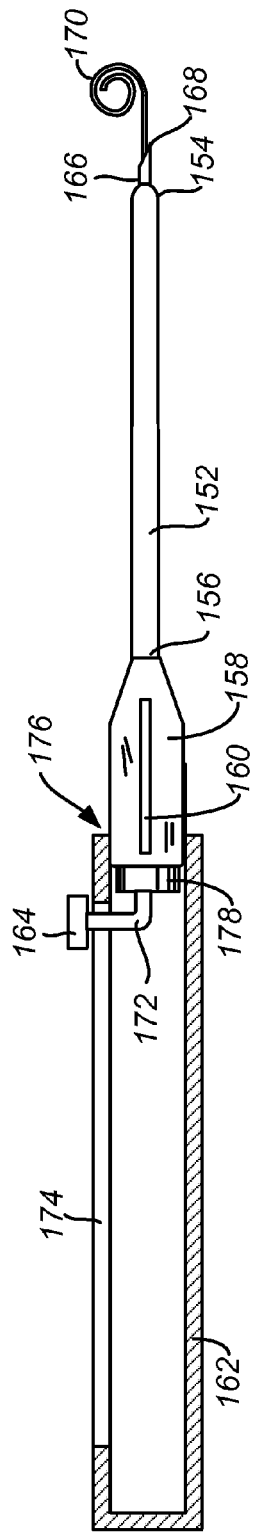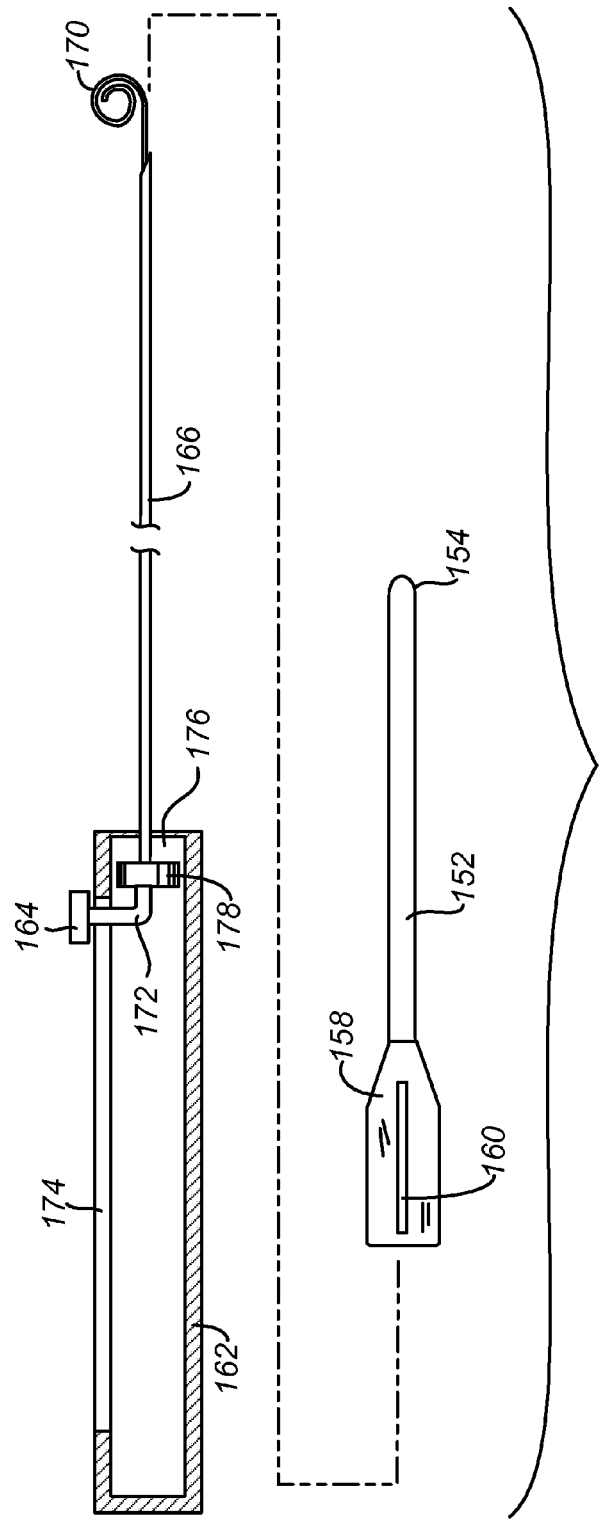

SYSTEMS AND METHODS FOR VENIPUNCTURE AND CATHETER PLACEMENT

CROSS-REFERENCE TO RELATED APPLICATIONS

This application claims priority to U.S. Provisional Patent Application No. 61/772,980, filed Mar. 5, 2013, and to U.S. Provisional Patent Application No. 61/758,517, filed Jan. 30, 2013, each of which is incorporated herein by reference in their entireties.

BACKGROUND OF THE INVENTION

1. Field of the Invention

The present invention relates generally to methods and systems for performing venipuncture. More particularly, the present invention provides a catheter and needle assembly with an integrated guidewire for transcutaneous insertion of the catheter into a patient's vein.

The term "venipuncture" refers generally to the process of obtaining intravenous access for any one of a variety of purposes, including intravenous infusion, therapy, blood sampling, and the like. In the hospital, for example, venipuncture is commonly used to place a small intravenous catheter for delivering intravenous fluids, drug delivery, blood sampling and the like.

While venipuncture and intravenous access in relatively healthy patients can be a simple matter, such access is often needed in patients who are not healthy and may have small, tortuous, collapsed, fragile, and/or difficult to locate veins. In such patients, venipuncture and intravenous access can be very challenging, particularly to less experienced phlebotomists, paramedics, nurses, and other health care practitioners.

In addition to difficult access, many intravenous catheter placement systems can result in accidental punctures and/or accidental needle contamination during or after placement of the intravenous catheter.

A particularly effective intravenous catheter placement device is described in commonly owned U.S. Patent Publ. 2008/0300574. This patent describes a catheter placement device which includes a handle having mechanism for advancing a guidewire through an access needle which carries the catheter where the handle is adapted to automatically retract both the needle and the guidewire from the catheter after the placement procedure is complete. While the catheter placement device has an effective and valuable design, the need to employ a relatively complex deployment handle increases the device's cost and complexity. Additionally, the handle can obscure the presence and status of the needle and guidewire components of the tool, thus making use of the insertion tool less intuitive.

For these reasons, it would be desirable to provide improved methods, systems, and tools for deploying intravenous catheters using needles and guidewires. It would be particularly desirable to provide simplified deployment systems and assemblies having fewer components and, even more desirably, to provide components which are clearly visible to the user and configured to be utilized and manipulated in a straightforward, intuitive manner. At least some of these objectives will be met by the inventions described below.

2. Description of the Background Art

Intravenous catheter insertion devices and methods are described in U.S. Pat. Nos. 5,704,914 and 5,800,395 and in commonly owned U.S. Patent Publs. 2010/0094310; 2010/0210934; and 2012/0197200, the full disclosures of which are incorporated herein by reference.

SUMMARY OF THE INVENTION

The present invention provides improved methods, systems, and assemblies for performing venipuncture, in particular for placing intravenous catheters at a target location in a patient's vein. While the methods, systems, and assemblies will be particularly useful for placement of peripheral venous catheters, such as by placement in a vein on a hand or an arm, they can also be useful with placement of a central venous catheter by insertion into a central vein, such as the internal jugular vein on the neck or the subclavian vein on the chest. The methods, systems, and assemblies could, in some instances, even be useful with placement of a catheter in a central or other artery, but such placement is not a principal purpose of the present invention.

An intravenous catheter assembly in accordance with the principles of the present invention comprises a tubular catheter body, an access needle, a guidewire, and a slide for deploying the guidewire. The tubular catheter body has a distal end, a proximal end, and at least one lumen therebetween. The access needle has a tissue-penetrating distal tip and usually a lumen therethrough. In a first embodiment, the guidewire is disposed in the lumen of the access needle. In a second embodiment, the guidewire is disposed outside of but in parallel to the access needle, typically riding in an axial groove formed in the exterior of the needle. In both embodiments, the guidewire has a distal tip configured to extend distally of the catheter to facilitate advancement of the catheter in the vasculature, as will be described in more detail below. The distal tip will frequently be in the form of a safety tip, such as a coiled safety tip as described in U.S. Patent Publ. 2008/0300574, the full disclosure which has previously been incorporated herein by reference.

In a first embodiment, the slide of the catheter assembly is slidably disposed over an exterior of a proximal region of the access needle and is coupled to a proximal end of the guidewire. In this way, the guidewire may be distally advanced by sliding the slide forwardly or distally over the access needle in order to position the distal tip of the guidewire beyond the distal end of the catheter. Once in this configuration, the access needle can be fully or partly retracted, or left in place without retraction, and the catheter and the distally projecting guidewire can be advanced in tandem to position the distal end of the catheter body at a target site in the venous or other vasculature. By advancing the catheter and the projecting guidewire in tandem, the guidewire acts as a "fixed" guidewire tip, further simplifying the catheter placement protocol of the present invention. The projecting wire will inhibit the distal tip of the catheter from sticking or kinking on an internal wall of the blood vessel.

In a second embodiment, the catheter assembly further includes a housing attached to a proximal end of the access needle, where the slide is disposed over the housing. The access needle is fixedly secured to a distal end of the housing, and the catheter is detachably secured to the distal end of the housing. In this way, the slide can be used to advance the guidewire beyond the distal ends of the catheter and the access needle, and the housing, access needle and guidewire may be detached and removed from the catheter after the catheter is in place at a desired location in the vein.

In a third embodiment, a proximal region of the catheter is disposed within the housing, and the proximal end of the catheter and a proximal end of the access needle may be configured to be engaged by the slide to advance the catheter and needle in tandem with the guidewire relative to the housing after the guidewire has been extended distally beyond the distal end of the catheter.

Coupling the guidewire to the slide can be accomplished in any manner which allows advancement or retraction of the slide to impart an equivalent advancement or retraction of the guidewire through the needle lumen. When the guidewire is disposed exteriorly of the access needle, the slide can be directly connected to a proximal end of the guidewire with minimum interference from the access needle. When the guidewire is disposed in the access needle lumen, then the coupling will need to penetrate the needle. For example, the slide and the guidewire could be coupled through a magnetic coupling which would not require any slot or passage in the needle. Both the slide and a proximal portion of the guidewire could carry magnetic elements and the needle could be formed of a non-magnetic material, such as a non-magnetic stainless steel, and the magnetic elements could couple through the wall of the needle. More typically, however, a slot or other axial passage will be formed in the needle allowing the slide to be coupled to the guidewire by a physical link which passes through the slot. In the illustrated embodiments, the link is formed simply by bending a proximal end of the guidewire at an angle which allows it to pass through the slot and be embedded or otherwise attached to the slide.

As further shown in the illustrated embodiments, the slot on the access needle will usually be closed at both a distal and a proximal end to define a specific length of travel through which the slider (and hence the guidewire) can be advanced and retracted. Thus, the distance between the two ends of the slot will define the maximum length of travel for the guidewire.

In embodiments having a housing, a proximal end of the guidewire may extend into the housing beyond the proximal end of the needle. As described above, a proximal end of the needle may be attached to a distal end of the housing and not extend into the housing. In such cases, the slide can be coupled to the needle within the housing, and the needle need not have a slot to allow such coupling. The needle, of course, could extend within the interior of the housing and coupling to the slide could be achieved as described previously for embodiments without housings.

The intravenous catheter assembly just described will preferably have at least two configurations. In a first configuration, the distal tip of the access needle extends beyond the distal end of the catheter body by a distance in the range from 0.1 mm to 20 mm, preferably from 1 mm to 5 mm. The distal tip of the guidewire remains retracted in the access needle, and the slider is retracted proximally from the proximal end of the proximal hub by a distance in the range from 10 mm to 100 mm, preferably from 15 mm to 35 mm. This first configuration is useful for initially advancing the catheter and needle into a target vein with the guidewire retracted. In a second configuration, the distal tip of the access needle may be left in placed (extended beyond the catheter tip) or may be retracted, and the slide is advanced distally to the proximal end of the catheter body to, in turn, advance the distal tip of the guidewire distally of the distal end of the catheter body and/or access needle by a distance in the range from 5 mm to 100 mm, usually from 10 mm to 35 mm. The access needle and guidewire will typically be capable of being withdrawn together from the catheter after the guidewire has been advanced into the catheter body lumen.

In specific aspects of the present invention, the tubular catheter body will have a proximal hub with a hemostasis valve, optionally having a side tube. The access needle is adapted to slidably extend through the hemostasis valve so that the needle may be introduced into a target vein or other blood vessel with the hemostasis valve reducing the blood loss. In other preferred aspects, the slider will have a distal face which mates with a proximal face of the proximal hub and/or the hemostasis valve when the slider is fully advanced distally to extend the guidewire. Usually, the slider will detachably lock to the hub when the distal face mates with the proximal face.

In another aspect of the present invention, a method for introducing an intravenous catheter to a target location in a vein of a patient comprises penetrating a distal tip of an access needle which carries the catheter into the vein. A guidewire is then advanced through a lumen of the needle by a short distance distally beyond a distal tip of the catheter within the vein. After the guidewire has been advanced, typically through the lumen of the needle, the access needle may be retracted proximally (or not) leaving the guidewire in place. The guidewire is optionally coupled to the catheter, and the guidewire and catheter, and the guidewire and catheter then advanced in tandem (simultaneously) to position the distal tip of the catheter at the target location, preferably by holding the wings of the catheter hub. Once the catheter is properly located, the access needle and the guidewire are withdrawn completely from the catheter, leaving the catheter in place for a desired medical protocol.

In specific aspects of the method, penetrating comprises penetrating both the distal tip of the access needle and the distal end of the catheter so that they lie in the vein prior to advancing the guidewire a short distance distally beyond the distal tip of the guidewire. Advancing the guidewire typically comprises advancing a slider coupled to the guidewire over the access needle, usually coaxially over the access needle. The guidewire and the slider are coupled so that advancing the slider will in turn cause the guidewire to advance by a like distance. Of course, advancing the catheter will also advance the guidewire. Coupling may be achieved in any conventional manner as described above. Coupling can be by direct attachment when the guidewire is exterior of the access needle. Alternatively, when the guidewire is present in the access needle lumen, the slider may be coupled to the guidewire magnetically or more usually by a link which travels through a slot formed in the needle. Typically, the slider engages the proximal hub after the slider is fully advanced in a distal direction and prior to advancing the guidewire and the catheter in tandem. When engaged, the slider may optionally be locked to the hub to help assure that the advancement of the guidewire and catheter will be simultaneous and in tandem. Any locking will usually be detachable but could be permanent or semi-permanent since the slider and guidewire will usually be withdrawn and disposed of together with the access needle.

In alternative aspects of the methods of the present invention, a proximal region of the catheter may be disposed within a housing and the slide may be located on the housing and used to engage a proximal end of the catheter and a proximal end of the access needle to advance the catheter and needle in tandem with the guidewire relative to the housing after the guidewire has been extended distally beyond the distal end of the catheter. The slider may be used to fully advance the guidewire relative to the access needle prior to advancing the guidewire, access needle and catheter in tandem.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 is an axial cross-sectional view of the intravenous catheter and needle assembly of FIGS. 1 and 2.

FIG. 3A is a cross-sectional view taken along line 3A-3A in FIG. 3.

FIG. 3B is an alternative cross-sectional view similar to that shown in FIG. 3A but showing the guidewire exterior to the access needle and traveling in an axial groove formed in a wall of the access needle.

FIGS. 6A-6C illustrate the intravenous catheter of FIG. 5 showing and access needle and a guidewire in different stages of advancement.

FIGS. 7A and 7B illustrate an alternate embodiment of the catheter advancement mechanism of a catheter of FIG. 5.

FIGS. 9A-9D illustrate the catheter of FIG. 8 showing the catheter, needle, and guidewire in various stages of advancement relative to a handle.

DETAILED DESCRIPTION OF THE INVENTION

Figure 1:
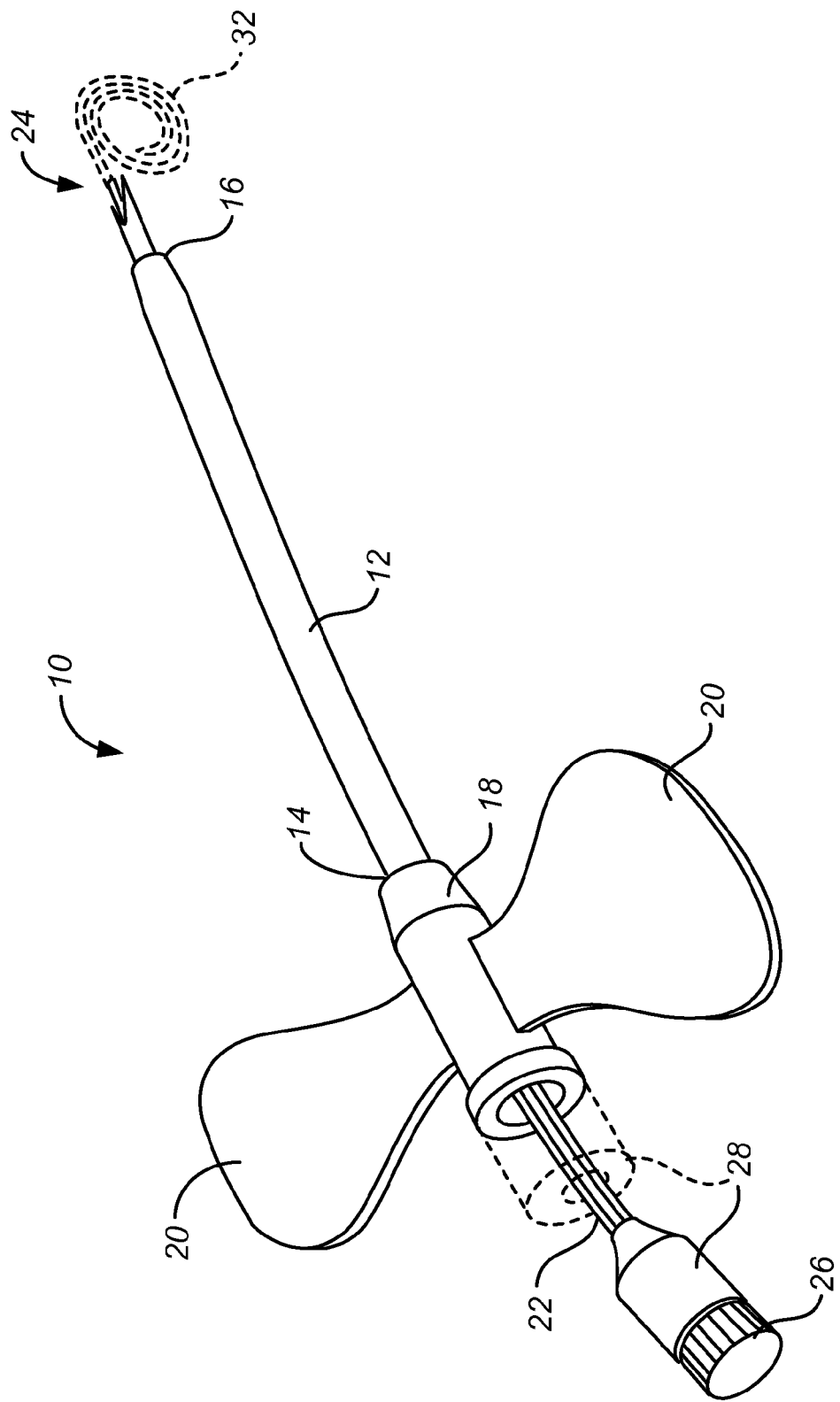
FIG. 1 is a perspective view of an intravenous catheter and needle assembly constructed in accordance with the principles of the present invention.
Figure 2:
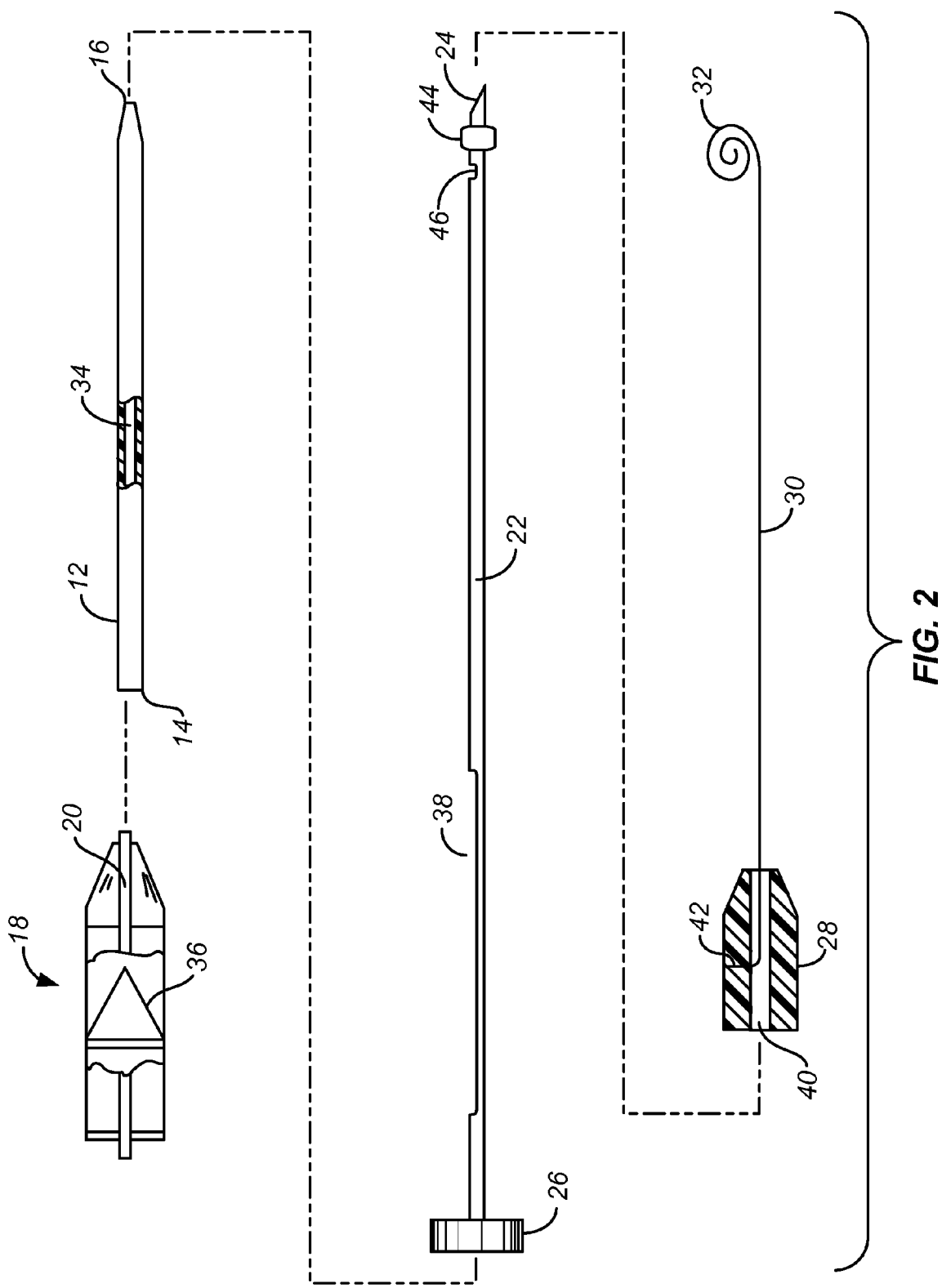
FIG. 2 is an exploded view of the intravenous catheter and needle assembly of FIG. 1.

As shown in FIGS. 1-3, an exemplary intravenous catheter and needle assembly 10 constructed in accordance with the principles of the present invention comprises a catheter body 12 having a proximal end 14 and a distal end 16. A proximal hub 18 is attached to the proximal end 14 of the catheter body and includes a pair of attachment wings 20 which are used to secure the catheter hub to a patient's skin in the conventional manner after the catheter has been introduced into a target vein or other blood vessel.

The catheter body 12 has a central lumen 34 (FIG. 2) which slidably receives an access needle 22 having a tissue-penetrating distal tip 24 which extends distally from the distal end 16 of the catheter body 12 when the assembly is ready for use. The tissue-penetrating tip will usually be a sharpened needle-type or trocar-type tip but could alternatively be a radiofrequency electrode or other energy-enhanced penetrating element. A proximal grip 26 is attached to a proximal end of the needle 22 so that a user can grip and hold the needle as a slider 28 is advanced over the needle, as will be described in more detail below. The slider 28 is attached to a proximal end of a guidewire 30 (FIG. 2), and the guidewire 30 usually has a safety tip 32 at its distal end, typically being a planar coil as illustrated. The proximal hub 18 will usually have a hemostasis valve 36 in its interior where the hemostasis valve can receive the needle 22, as best seen in FIG. 3.

The slider 28 will be slidably mounted over the exterior of the needle 22, as best seen in FIG. 3. The guidewire 30 will be present in a central passage (not shown) of the access needle, and the slider 28 is slidably mounted over a proximal portion of the needle. A link 42 attached to the slider 28 passes through a slot 38 in the proximal region of the needle so that translation of the slider 28 in a distal direction causes distal tip 32 of the guidewire to advance axially out the distal tip 24 of the needle, as shown in broken line in FIG. 1, while retraction of the slider 28 and a proximal direction fully withdraws the guidewire into the needle so that the guidewire is not visible outside of the needle.

When the access needle 22 is introduced into the lumen 34 of the catheter 12, as shown in FIG. 3, a distal seal 44 which is coaxially disposed over a distal portion of the needle seats at a distal end of the lumen 34 of the catheter to properly position the needle so that a short distal segment, typically in the range from 0.1 mm to 20 mm, preferably from 1 mm to 5 mm, extends distally beyond the distal end 16 of the catheter, as shown in FIG. 3. A blood perfusion port 46 is formed in the needle just proximally of the seal 44 so that blood entering the distal tip 24 of the needle (when the needle is introduced to a vein or other blood vessel) will flow out through the port 46 and provide a blood flow to a visible region in the hub 18 or catheter body so that "flash back" occurs and the user knows that the needle has entered the vein. Blood will generally be contained within the hub 18 by the hemostasis valve 26.

Referring now to FIG. 3A, guidewire 30 will usually travel in lumen 31 of the access needle 30. As an alternative, however, guidewire 30 could travel in a axial groove 33 formed in the wall of the access needle.

Figure 4A:
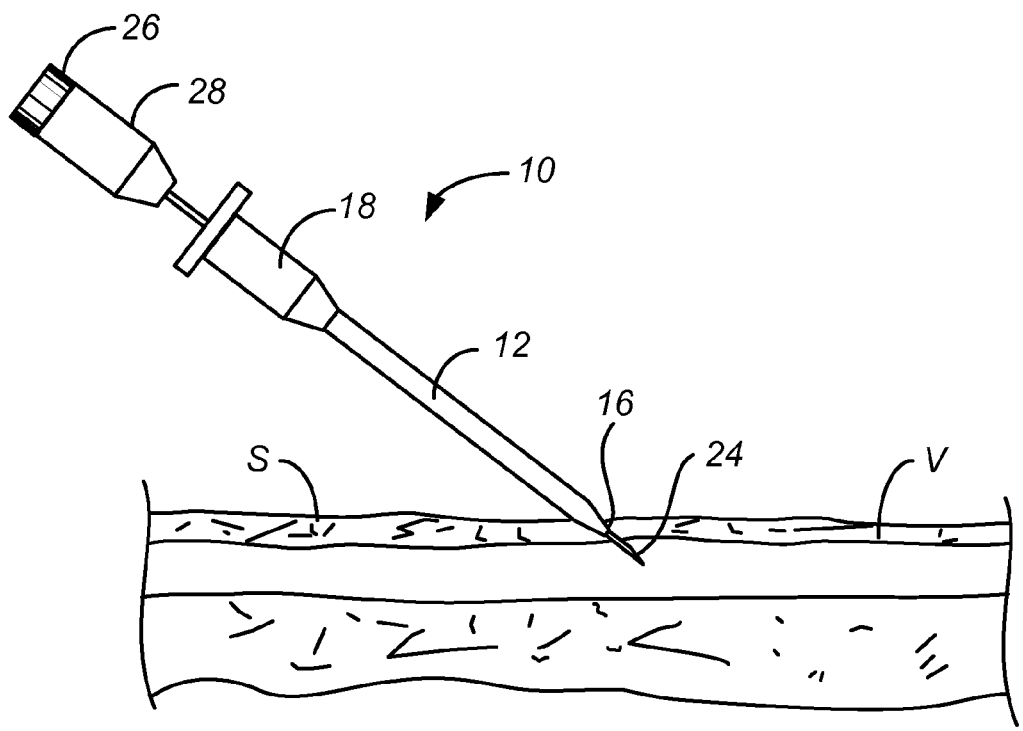
FIGS. 4A through 4D illustrate use of an intravenous catheter and needle assembly for introducing a catheter into a vein in accordance with the principles of the methods of the present invention.
Figure 4B:
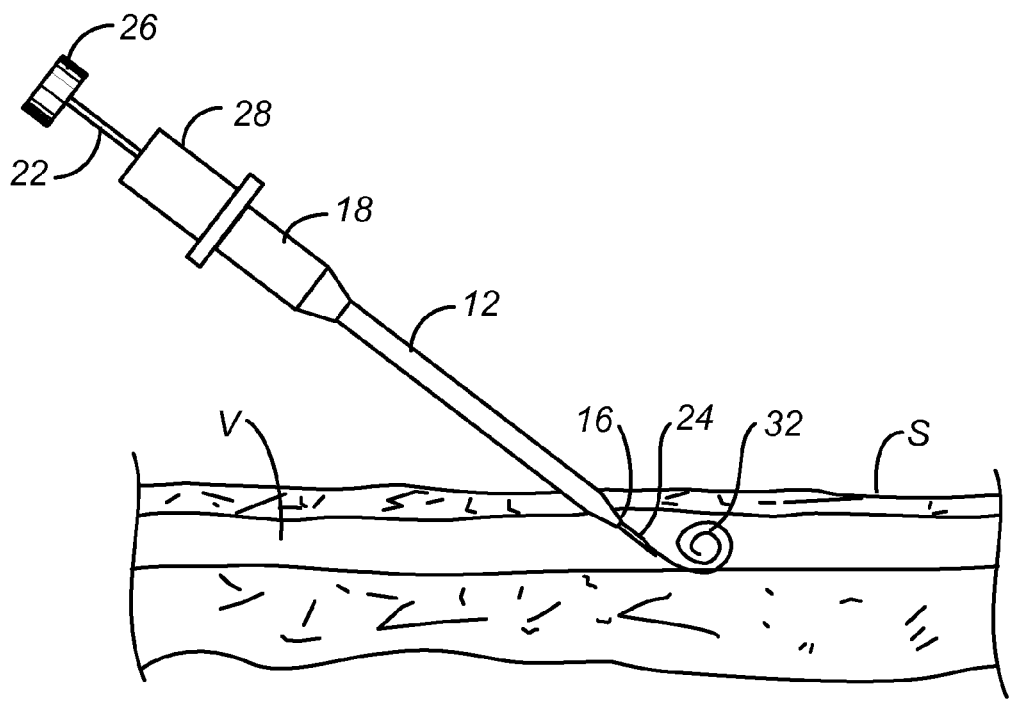
Figure 4C:
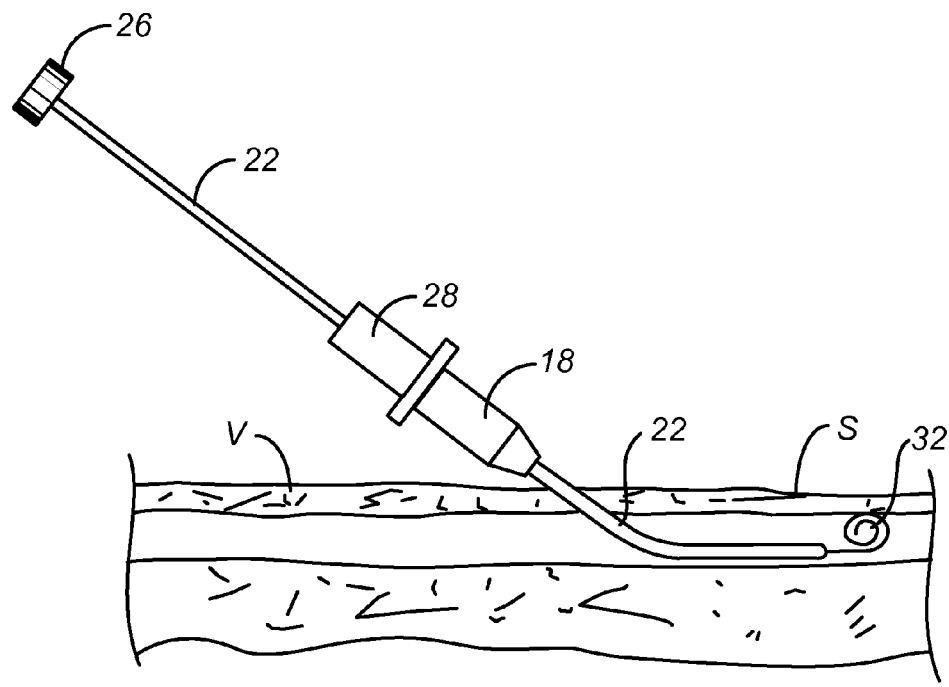
Figure 4D:
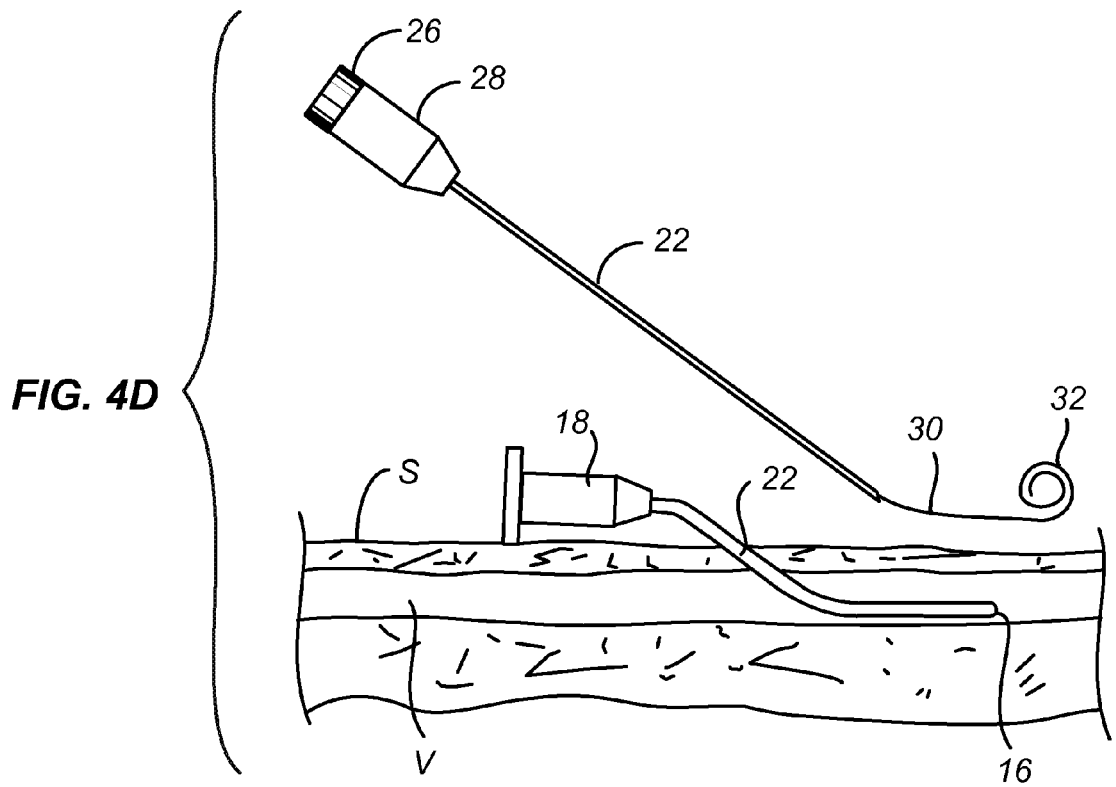

Referring now to FIGS. 4A through 4D, use of the intravenous catheter and needle assembly 10 for placing the catheter 12 within a vein V will be described. The catheter needle assembly 10 is initially in its "shelf" configuration with the distal end 24 of the needle extending distally of the distal end 16 of the catheter body and the guidewire (not shown) fully retracted within the interior of the needle. The user can manipulate the assembly by holding hub 18 and inserting the distal tip 24 of the needle through the patient's skin S into a desired vein V until flash back is observed, as shown in FIG. 4A. Once flash back is observed and it is confirmed that the needle tip is in the vein, the safety tip 32 of the guidewire may be advanced by distally moving the slider 28 until a distal surface of the slider engages a proximal surface of the hub, as shown in FIG. 4B. After the safety tip 32 has been advanced, the needle can be partially or fully retracted (with full retraction defined by the link 42 engaging a proximal end of slot 38), and the catheter 28 can be advanced in tandem with the needle safety tip 32 limiting the risk of accidental perforation or other trauma. The safety tip 32 will be, in effect, locked in place by engagement of the slider 28 and the hub 18 so that the catheter 22 and safety tip are advanced in tandem until the catheter tip 16 reaches a desired or target location in the vein V, as shown in FIG. 4D. Once the distal end of the catheter 16 is in its desired location, the sub-assembly of the needle 22 and guidewire 30 may be fully withdrawn, as shown in FIG. 4D, and the proximal hub 18 secured to the patient's skin S, typically using the attachment wings 20 shown in FIG. 1. At this point, the catheter 22 and hub 18 are in place and ready for use in introducing fluids, taking samples, introducing drugs, or any other desired purpose.

Referring now to FIGS. 5, 6A-6C, and 7A-7B, a second embodiment of a catheter and needle assembly 100 constructed in accordance with the principles of the present invention will be described. The catheter and needle assembly 100 includes a catheter body 102 having a proximal end 104, a distal end 106, and a proximal hub 108 attached to the proximal end. A pair of attachment wings 110 are secured to opposite sides of the proximal hub 108, and a housing 112 is detachably secured to a proximal end of the hub 108. The housing carries a slider 114, and the housing can serve as a handle or manipulation tool for the catheter and needle assembly 100.

Referring now in particular to FIGS. 6A-6C, an access needle 118 extends from a proximal end of the housing 112 and passes through a central lumen of the catheter body 102. A distal tip 116 of the access needle extends distally just beyond the distal end of the catheter body 102, typically by distance of 1 mm to 10 mm, usually from 2 mm to 5 mm. The access needle 118 slidably passes through a hemostasis valve 122, and the proximal end of the needle 118 is fixedly secured to or within the housing. In this way, the needle will remain stationary relative to the housing when the catheter hub 108 is detached, as described in more detail below.

Figure 5:
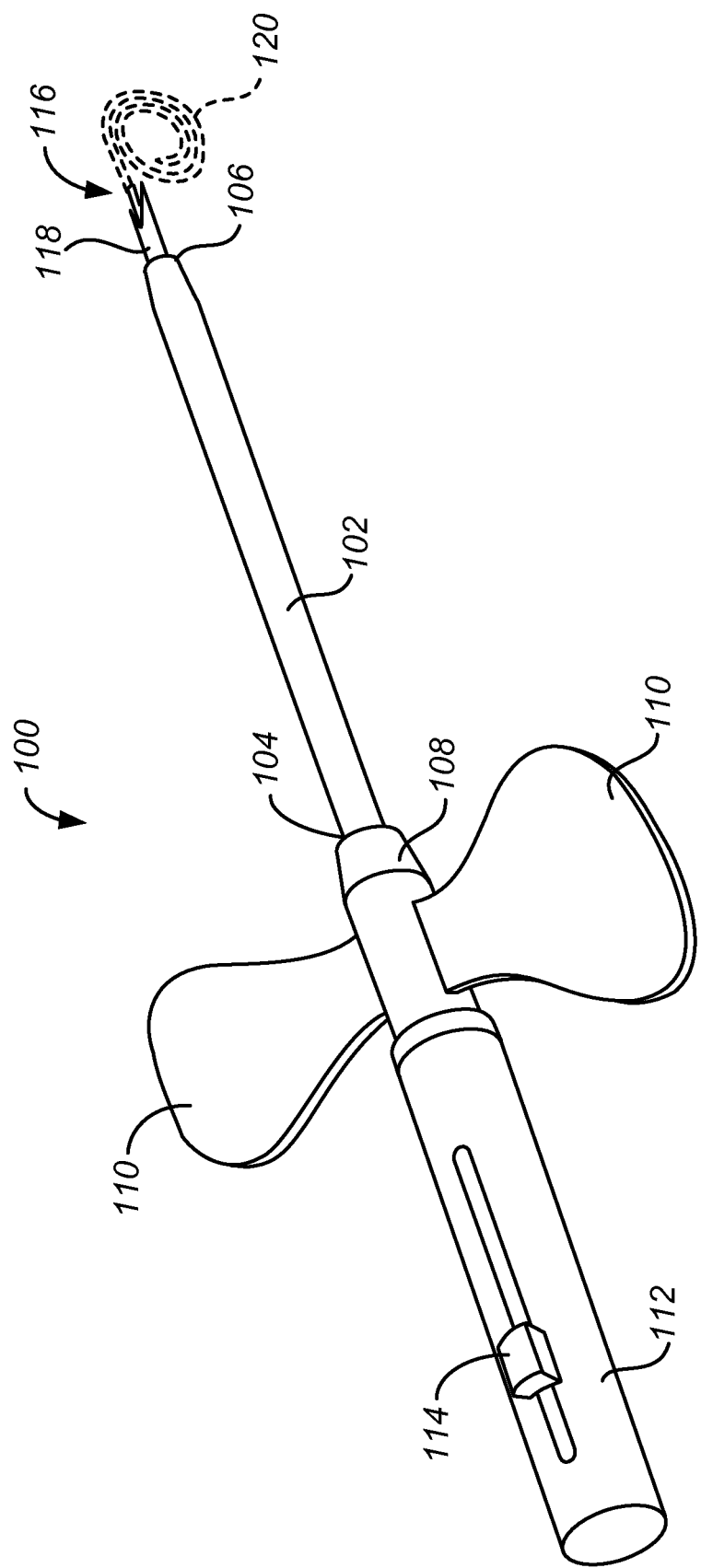
FIG. 5 is a perspective view of a second embodiment of an intravenous catheter and a needle assembly having a housing constructed in accordance with the principles of the present invention.
Figure 8:
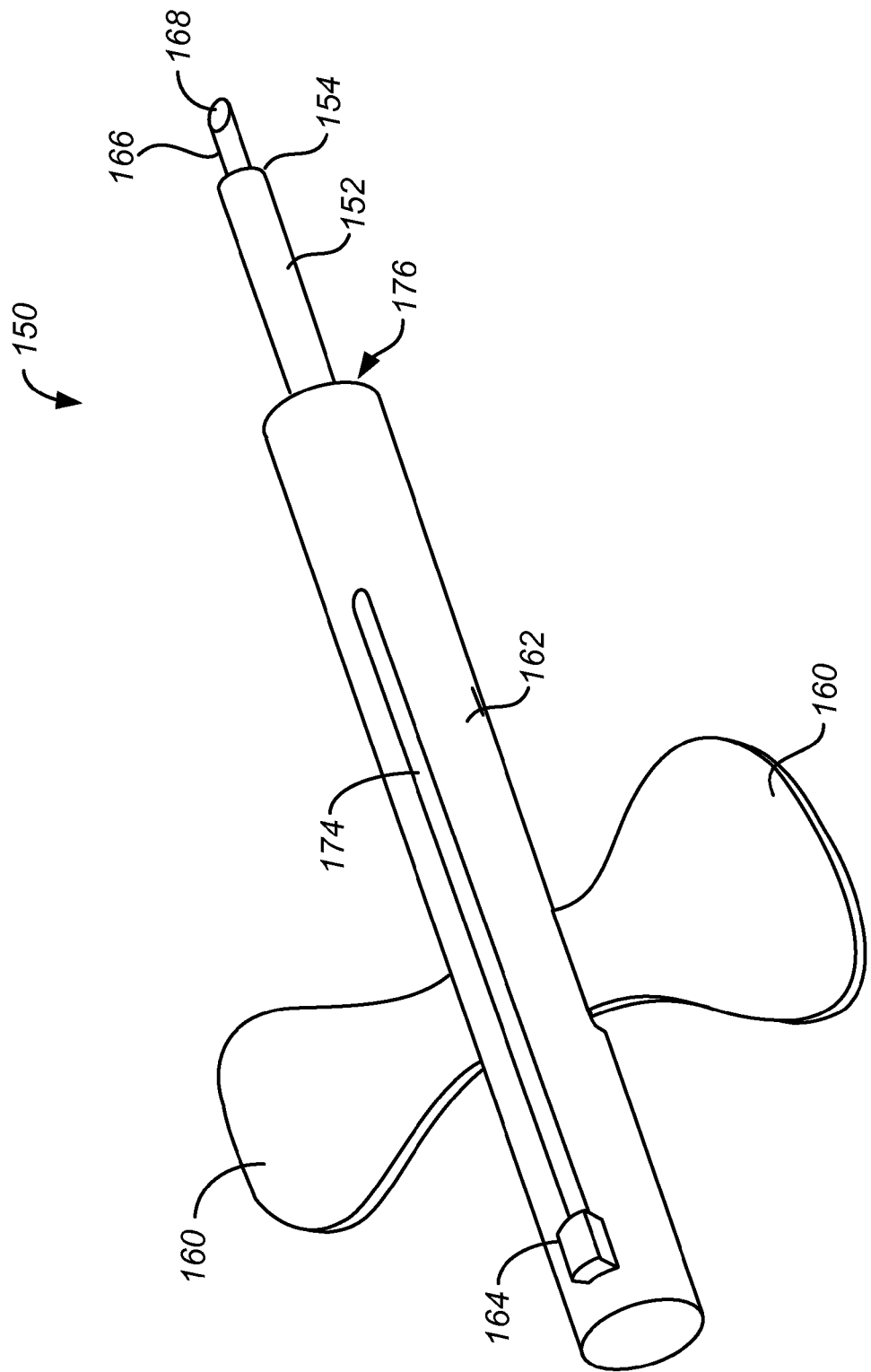
FIG. 8 is a perspective view of third embodiment of an intravenous catheter and needle assembly constructed in accordance with the principles of the present invention.

A guidewire 120 is attached to the slider 114 via a pin 124 or other suitable link or coupling number. The guidewire will typically have a coil or other safety tip, as best seen in FIG. 5. The guidewire tip is initially held within a lumen of the access needle 118, as shown in FIG. 6A. Once the slider 114 is partially advanced, as shown in FIG. 6B, the distal tip of the guidewire 120 will emerge from the distal end of 116 of the access needle 118. By further advancing the slider 114 in a distal direction, the guidewire 120 may be extended further, as shown in FIG. 6C.

As described with the prior embodiment, the guidewire 120 will typically be extended after the distal end 116 of the access needle 118 and the distal end 106 of the catheter body 102 have been advanced into a vein and blood flashback observed. After the guidewire is extended by a desired length using the slider 114, the assembly of the guidewire, access needle, and catheter may be advanced simultaneously and in tandem with the guidewire tip preventing the exposed needle tip 116 from injuring the vein. Once the catheter is in the desired position, the hub 108 may be detached from a distal end of the handle 112, as shown in broken line in FIG. 6C. The needle and guidewire may then be withdrawn from the lumen of the catheter leaving the catheter in place for subsequent use.

As shown in FIGS. 7A and 7B, a pair of engagement members 130 may be attached to the pin 124. Engagement members 130 could have a variety of configurations, but for convenience they are shown as elongated rods. The engagement members 130 are aligned with a pair of holes 132 at the distal end of the housing 112. Thus, as the slider 114 is initially advanced, the engagement members will advance within the housing over a preselected length. When the slider 114 is advanced, for example about half way through the housing as illustrated, the distal tips of the engagement members 130 will pass through the holes 132 and engage a proximal face of the hub 108. Thus, further advancement of the engagement members can detach the hub from the housing, as shown in FIG. 7B.

Referring now to FIGS. 8 and 9A-9D, a third embodiment of a catheter and needle assembly 150 and it's use will be described. The catheter and needle assembly 150 comprises a catheter having catheter body 152 with a distal end 154 and a proximal end 156 (best seen in FIGS. 9A-9B). A catheter of 158 is attached to the proximal end 156 of the catheter body, and a pair of attachment wings 160 are provided on the catheter hub, as generally described with the previous embodiments.

In contrast to the previous embodiments, the catheter hub 158 and proximal region of the catheter body 152 are received within an interior of a housing 162. A slide 164 is mounted in a slot 174 on the housing and is attached to a proximal end of a guidewire 170 by a pin 172 other coupling member so that distal advancement of the slide will cause the catheter to advance distally from an undeployed configuration (where it is fully within an interior lumen of access needle 166, as shown in FIG. 9A) to a deployed configuration (where it has advanced distally beyond a distal end of access needle 166, as shown in FIG. 9B).

The sequence of guidewire and catheter deployment is best understood by observing the differences between FIGS. 9A and 9B. In FIG. 9A, both the catheter 152 and the guidewire 170 are undeployed, and the catheter needle assembly 150 is ready to be introduced into a vein of a patient. A user can manipulate the housing 162 as a handle and can access the patient vein in a conventional manner, typically by observing blood feedback to confirm that the tip 168 of the needle 166 has entered the vein.

Once inside the vein, the user may hold the housing stationary and advance the slider 164 sufficiently to deploy a tip, typically a safety tip of the guidewire 160, as shown in FIG. 9B. The user may then manipulate the housing to advance the catheter may with the guidewire 170, needle 166, and catheter body 152 remaining stationary relative to each other. The safety tip of the guidewire prevents the needle tip from damaging the vein.

In order to expose the entire length of the catheter body 152 for introduction into the vein, the slider 164 will be fully advanced to the distal direction within the slot 174, as shown in FIG. 9C. The assembly including the housing 162, catheter body 152, access needle 166, and guidewire 170 may then be advanced until the distal end 154 of the catheter reaches the desired location within the patient vein. At that point, the housing may be pulled off the catheter and the hub 158 released through the open end 176 of the housing. A proximal end of the needle 166 will be secured in a sliding needle disc 178 so that the needle remains attached to the housing 162 and the needle and guidewire 117 may be removed together from the lumen of the catheter body 152, leaving the catheter in place ready for use.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An intravenous catheter assembly, comprising:
a tubular catheter body having a distal end, a proximal end, and a lumen therebetween;
an access needle disposed in the tubular catheter body lumen and having a tissue-penetrating distal tip extending distally beyond the distal end of the tubular catheter body;
a guidewire having a portion disposed outside and in parallel to the access needle and having a distal tip, wherein the access needle and the guidewire may be withdrawn together from the tubular catheter body after the guidewire has been advanced in the tubular catheter body lumen;
a slide coupled to a proximal end of the guidewire so that distal advancement of the slide advances the distal tip of the guidewire from a distal end of the access needle;
a first configuration, wherein:
the distal tip of the access needle extends beyond the distal end of the tubular catheter body by a distance in a range from 0.1 mm to 20 mm, and
a proximal end of the slide is retracted from the proximal end of the tubular catheter body by a distance in a range from 10 mm to 100 mm; and
a second configuration, wherein the distal tip of the guidewire extends beyond the distal end of the tubular catheter body by a distance in a range from 5 mm to 100 mm.

2. The assembly according to claim 1, wherein the slide is disposed over a proximal region of the access needle.

3. The assembly according to claim 1, further comprising a housing attached to a proximal end of the access needle, wherein the slide is disposed over the housing.

4. The assembly according to claim 3, wherein the access needle is fixedly secured to a distal end of the housing and the tubular catheter body is detachably secured to the distal end of the housing, wherein the slide advances the guidewire beyond the distal end of the catheter and wherein the housing, access needle and guidewire may be detached and removed from the catheter after the catheter is in place.

5. The assembly according to claim 4, wherein a proximal region of the catheter is disposed within the housing and wherein the proximal end of the catheter and the proximal end of the access needle are configured to be engaged by the slide to advance the catheter and needle in tandem with the guidewire relative to the housing after the guidewire has been extended distally beyond the distal end of the catheter.

6. The assembly according to claim 2, wherein the access needle has a lumen and the guidewire is slidably disposed in the access needle lumen.

7. The assembly according to claim 6, wherein the access needle has an axial slot and the proximal end of the guidewire is connected to the slide through the axial slot.

8. The assembly according to claim 7, wherein the axial slot is closed over distal and proximal regions of the access needle.

9. The assembly according to claim 8, wherein a link between the guidewire and the slide is disposed in the slot with a length of travel defined by closed ends of the slot.

10. The assembly according to claim 1, wherein the access needle has an exterior axial groove and the guidewire is slidably disposed in the exterior axial groove.

11. The assembly according to claim 1, wherein the guidewire is slidably disposed within a lumen in the access needle.

12. The assembly according to claim 1, wherein the distal tip of the access needle remains extended in the second configuration.

13. The assembly according to claim 1, wherein the distal tip of the access needle is retracted in the second configuration.

14. The assembly according to claim 1, wherein the tubular catheter body has a proximal hub with a hemostasis valve, wherein the access needle slidably extends through the hemostasis valve.

15. The assembly according to claim 14, wherein the slide has a distal face which mates with a proximal face of the hemostasis valve when the slide is fully advanced distally to extend the guidewire.

16. The assembly according to claim 15, wherein the slide detachably locks to the proximal hub when the distal face mates with the proximal face.

17. An intravenous catheter assembly, comprising:
a tubular catheter body, including a proximal hub with a hemostasis valve;
an access needle disposed in a catheter body lumen and having a tissue-penetrating distal tip extending distally beyond a distal end of the tubular catheter body, wherein the access needle slidably extends through the hemostasis valve;
a guidewire having a portion disposed outside and in parallel to the access needle and having a distal tip;
a slide coupled to a proximal end of the guidewire so that distal advancement of the slide advances the distal tip of the guidewire from the distal end of the access needle, wherein the slide has a distal face which mates with a proximal face of the hemostasis valve when the slide is fully advanced distally to extend the guidewire.

18. The assembly according to claim 17, wherein the slide detachably locks to the proximal hub when the distal face of the slide mates with the proximal face of the hemostasis valve.

* * * * *